(12) United States Patent
Natarajan et al.

(10) Patent No.: US 10,720,942 B2
(45) Date of Patent: Jul. 21, 2020

(54) APPARATUS AND METHOD FOR DATA COMPRESSION IN A WEARABLE DEVICE

(71) Applicant: Intel Corporation, Santa Clara, CA (US)

(72) Inventors: Venkat Natarajan, Bangalore (IN); Nikita Pendekanti, Hyderabad (IN); Kumar Ranganathan, Bangalore (IN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/741,497

(22) PCT Filed: Jun. 1, 2016

(86) PCT No.: PCT/US2016/035335
§ 371 (c)(1),
(2) Date: Jan. 2, 2018

(87) PCT Pub. No.: WO2017/007546
PCT Pub. Date: Jan. 12, 2017

(65) Prior Publication Data
US 2019/0036545 A1 Jan. 31, 2019

(30) Foreign Application Priority Data
Jul. 3, 2015 (IN) .......................... 3411/CHE/2015

(51) Int. Cl.
*H03M 7/34* (2006.01)
*H03M 7/30* (2006.01)
(Continued)

(52) U.S. Cl.
CPC ......... *H03M 7/6047* (2013.01); *A61B 5/7232* (2013.01); *H03M 7/30* (2013.01);
(Continued)

(58) Field of Classification Search
CPC .. H03M 1/38; H03M 13/1122; H03M 13/114; H03M 13/1145; H03M 13/1148;
(Continued)

(56) References Cited

U.S. PATENT DOCUMENTS 7,288,066 B2 10/2007 Drew
8,504,894 B1 8/2013 Zeng et al.
(Continued)

FOREIGN PATENT DOCUMENTS

WO 2009087430 7/2009

OTHER PUBLICATIONS

International Search Report & Written Opinion dated Aug. 24, 2016 for PCT Patent Application No. PCT/US16/35335.
(Continued)

*Primary Examiner* — Linh V Nguyen
(74) *Attorney, Agent, or Firm* — Green, Howard, & Mughal LLP

(57) ABSTRACT

Described is an apparatus and method for data compression using compressive sensing in a wearable device. Described is also a machine-readable storage media having instruction stored thereon, that when executed, cause one or more processors to perform an operation comprising: receive an input signal from a sensor; convert the input signal to a digital stream; and symmetrically pad on either ends of the digital stream with a portion of the digital stream to form a padded digital stream.

25 Claims, 14 Drawing Sheets

(51) Int. Cl.
*H04L 1/00* (2006.01)
*A61B 5/00* (2006.01)
*A61B 5/024* (2006.01)
*A61B 5/0402* (2006.01)
*A61B 5/0476* (2006.01)

(52) U.S. Cl.
CPC ....... *H03M 7/3062* (2013.01); *H03M 7/6058* (2013.01); *H04L 1/00* (2013.01); *A61B 5/02416* (2013.01); *A61B 5/0402* (2013.01); *A61B 5/0476* (2013.01)

(58) Field of Classification Search
CPC .. H03M 13/116; H03M 1/185; H04W 72/042; H04W 76/14; H04W 72/1289; H04W 4/70; H04W 4/80; H04W 76/10; H04W 28/06; H04W 52/146
USPC ........... 341/51, 155; 375/227; 455/135, 161, 455/277.2
See application file for complete search history.

(56) References Cited

U.S. PATENT DOCUMENTS

| | | | | |
|---|---|---|---|---|
| 10,476,630 | B2* | 11/2019 | Cowell | H04L 1/003 |
| 2004/0135992 | A1* | 7/2004 | Munro | G01S 7/483 |
| | | | | 356/4.01 |
| 2004/0151478 | A1 | 8/2004 | Yoo et al. | |
| 2008/0055133 | A1 | 3/2008 | Chakrabartty | |
| 2009/0327847 | A1* | 12/2009 | Shen | H03M 13/1151 |
| | | | | 714/804 |
| 2010/0145691 | A1* | 6/2010 | Bellegarda | G10L 15/187 |
| | | | | 704/211 |
| 2010/0218066 | A1* | 8/2010 | Okamura | H03M 13/1105 |
| | | | | 714/752 |
| 2013/0155541 | A1* | 6/2013 | Feng | H03M 5/145 |
| | | | | 360/51 |
| 2013/0177004 | A1* | 7/2013 | Srinivasa | H04L 5/0091 |
| | | | | 370/338 |
| 2013/0227376 | A1* | 8/2013 | Hwang | H03M 13/05 |
| | | | | 714/776 |
| 2013/0315288 | A1* | 11/2013 | Weng | H04W 24/02 |
| | | | | 375/227 |
| 2014/0072069 | A1* | 3/2014 | Nammi | H04B 7/0486 |
| | | | | 375/267 |
| 2014/0258249 | A1 | 9/2014 | Ozturk et al. | |
| 2014/0307976 | A1* | 10/2014 | McLane | H04N 19/647 |
| | | | | 382/233 |
| 2014/0362098 | A1 | 12/2014 | Kerofsky | |
| 2016/0315733 | A1* | 10/2016 | Murakami | H04L 1/0057 |

OTHER PUBLICATIONS

Candes, et al. "An introduction to Compressive Sampling", IEEE Signal Processing Magazine, Mar. 2008, 10 pages.
Chae, D., et al. "Performance Study of Compressive Sampling for ECG Signal Compression in Noisy and Varying Sparsity Acquisition", IEEE International Conference on Acoustics, Speech and Signal Processing, 2013, 4 pages.
European Extended Search Report dated Feb. 1, 2019 for EP Patent Application No. 16821778.4.
Anonymous "Pad Array—Padarray", MATLAB Documentation—mathworks.com, Jun. 7, 2015, XP055543559, 3 pages. retrieved from the internet on Jan. 17, 2019: https://web.archive.org/web/20150607192238/https://www.mathworks.com/help/images/ref/padarray.html.
He, Z. et al., "The Simplest Measurement Matrix for Compressed Sensing of Natural Images", 2010 17th IEEE International Conference on Image Processing (ICIP 2010). Sep. 26-29, 2010, Hong Kong, CN, IEEE, Piscataway, NJ, USA, Sep. 26, 2010, pp. 4301-4304, XP031813306. ISBN: 978-1-4244-7992-4.
Ravelomanantsoa, A. et al., "Simple and Efficient Compressed Sensing Encoder for Wireless Body Area Network", IEEE Transactions on Instrumentation and Measurement, IEEE Service Center, Piscataway, NJ, US, V. 63, No. 12; Dec. 1, 2014, pp. 2973-2982, XP011563738; ISSN: 0018-9456, DOI: 10.1109/TIM.2014.2320393.
Ravelomanantsoa, A. et al., "Simple Deterministic Measurement Matrix: Application to EMG Signals", 2014 26th International Conference on Microelectronics (ICM), IEEE, Dec. 14, 2014, pp. 76-79, XP032756853, DOI: 10.1109/ICM.2014.7071810.
Examination Report from Indian Patent Application No. 3411/CHE/2015 notified Jan. 18, 2019, 5 pgs.

* cited by examiner

APPARATUS AND METHOD FOR DATA COMPRESSION IN A WEARABLE DEVICE

CLAIM OF PRIORITY

This Application is a National Stage Entry of, and claims priority to, PCT Application No. PCT/US16/35335, filed on 1 Jun. 2016, and titled "APPARATUS AND METHOD FOR DATA COMPRESSION IN A WEARABLE DEVICE", which claims priority to Indian Patent Application No. 3411/CHE/2015, filed 3 Jul. 2015, and titled "APPARATUS AND METHOD FOR DATA COMPRESSION IN A WEARABLE DEVICE", and which are incorporated by reference in their entirety for all purposes.

BACKGROUND

Electrocardiogram (ECG) and Photoplethysmogram (PPG) signals are used in wearable applications ranging from authentication to health and wellness. Although ECG and PPG signals can be measured on demand, continuous sensing of ECG/PPG signals in a Body Sensor Network (BSN) is a challenge. Continuous ambulatory monitoring of bio-signals is important to wearable applications ranging from healthcare and sports to biometric authentication. For example, continuous real-time ECG monitoring enables the monitoring of cardiac activity for extended periods (e.g., days), helps identify and mitigate potential risks, and improves wellness of the patient. Sports monitoring systems have begun to rely on continuous tracking of physiological signals for real-time performance enhancement.

However, real-time monitoring of bio-electric signals for long durations under free living conditions (e.g., on a wireless sensor node coupled to a running person) introduces stringent constraints such as enhanced battery life, efficient memory use on the wireless sensor node, noise-resilience, and adaptation to non-stationary properties of the continuously sampled signal. For example, continuous sampling of ECG signals at a rate of 500 bytes/s results in several megabytes of data in a span of a few hours.

BRIEF DESCRIPTION OF THE DRAWINGS

The embodiments of the disclosure will be understood more fully from the detailed description given below and from the accompanying drawings of various embodiments of the disclosure, which, however, should not be taken to limit the disclosure to the specific embodiments, but are for explanation and understanding only.

DETAILED DESCRIPTION

Figure 1A:
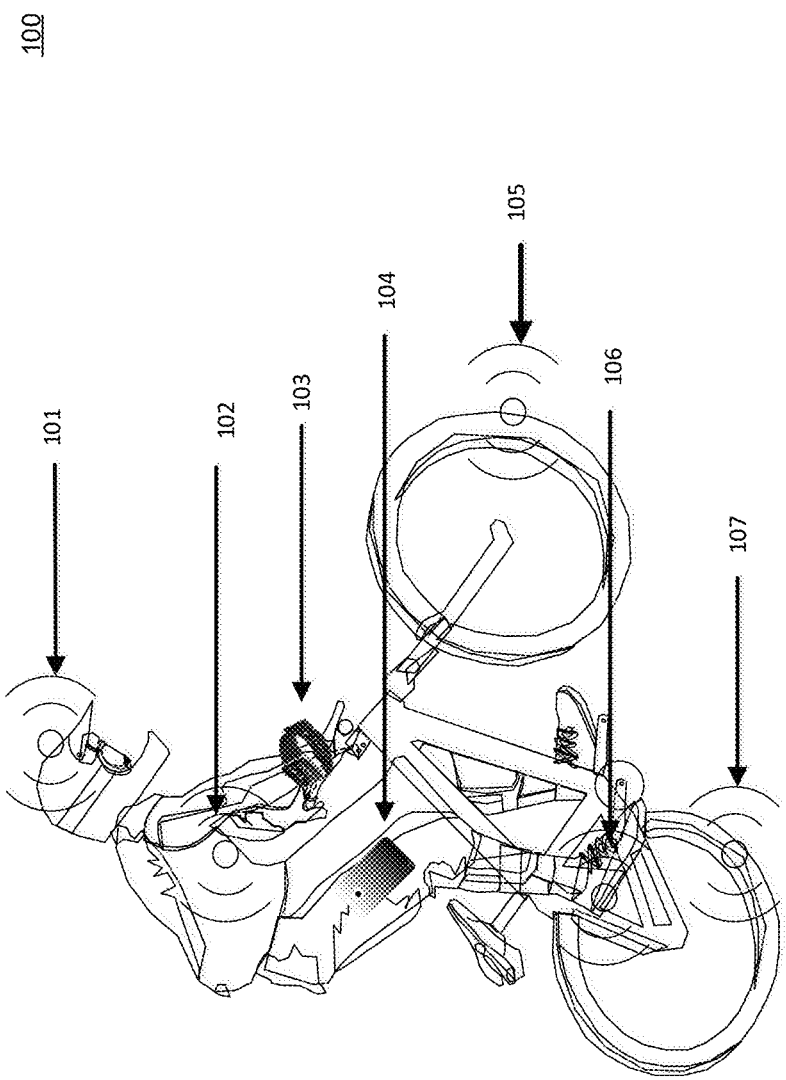
FIG. 1A illustrates an ensemble of wearable devices including one or more sensor nodes having an apparatus for continuous Compressive Sensing (CS) of signals, according to some embodiments of the disclosure.

Traditionally, the process of Compressive Sensing (CS) applied a random Gaussian sensing matrix to encode an input bio-electric signal (e.g., an Electrocardiogram (ECG) signal). The random Gaussian matrix, however, is dense and requires relatively large onboard memory with high compute capability, and is difficult to embed in a resource-constrained wireless sensing node. Hence, alternate sensing matrix types with different distributions and compact structure have been proposed.

For example, Toeplitz, circulant, and triangular sensing matrices for CS of ECG signals have been investigated for efficacy and power savings. However, embedding these matrices in a resource-constrained node is challenging because the random elements of the sub-matrix need to be generated onboard the sensor node. Pre-calculating and storing of these matrices is impractical and of limited use because the encoding logic and matrix structure need to adapt to variations in the sampled signal and scale to different types of bio-signals (e.g., ECG, Photoplethysmogram (PPG), EEG (electroencephalography) signals).

The use of a Binary Permuted Block Diagonal (BPBD) sensing matrix simplifies the hardware implementation of the encoding algorithm. At the same time, BPBD matrix provides high sensing efficiency with accurate reconstruction. One limitation from prior studies using the BPBD matrix is that the compression curve is highly discontinuous with constraints on possible compression ratios (CR). For example, compression ratio using prior art BPBD matrix can only be of 2, 4, 8, 16 . . . etc. for an input signal of 512 samples. As such, compression ratio using prior art BPBD matrix forms a discontinuous compression curve. Compression ratio can be expressed as a ratio of input to output bits as follows:

$$\text{Compression Ratio, } CR = \frac{\text{Input bits}}{\text{Output bits (transmitted)}}$$

In a Body Sensor Network (BSN), however, where signals are continuously sampled from several sensors, there is a need for flexibility to operate at any point on a continuous compression ratio curve for optimal performance without being constrained by a limited set of feasible compression design points.

One mechanism for compression is the Discrete Wavelet Transform (DWT) algorithm. DWT gives high compression with low signal loss. However, DWT algorithm is computationally demanding, memory intensive, and consumes a significant amount of energy. Furthermore, to embed DWT based mechanism on a resource-constrained wireless sensor node (e.g., System-on-Chip (SoC)), other constraints such as fixed point implementation for low power, embed code in finite memory, use of appropriate data types for computational accuracy, optimization of the algorithm for power and run time etc. need to be overcome. These challenges make DWT compressing mechanisms less attractive for such applications.

From a system implementation perspective, dynamically selecting the right compression parameter (i.e., dynamically selecting a target compression ratio for a specific signal and application under consideration) is a challenge. For example, non-critical applications, such as, wellness and gaming can tolerate higher reconstruction loss, thus, allowing higher compression ratios in contrast to medical applications that require low reconstruction loss with lower compression ratios permissible. Reconstruction loss is a metric that refers to a difference between the input signal (i.e., the uncompressed signal) and the output reconstructed signal. Reconstruction loss can be expressed as a percentage difference of the input and output signals.

In a wearable system, the sensor nodes sample multiple bio-signal channels simultaneously, each requiring compression, and a designer must automatically set the compression parameters for each channel in real-time. Hence, the compression algorithm is desired to adapt to signal variations in ambulatory monitoring, handle different types of bio-signals on a BSN, and meet the signal quality requirements for different applications on the gateway device.

Real-time diagnostics in free-living conditions as well as continuous authentication generates large amounts of streaming data that quickly decreases sensor node battery life, saturates wireless bandwidth, and demands large data storage. Increased battery life can be achieved by reducing data traffic from the sensor node, for example, via real-time compression. Compression techniques such as Random Gaussian based compressive sensing algorithm may not be suitable for application in a BSN as it may not be embeddable in power and memory constrained edge System-on-Chips. Also, DWT algorithm consumes too much power making longevity of battery life a challenge.

Some embodiments describe a power-efficient technique to deliver high compression of continuously sensed input signals (e.g., bio-signals such as ECG/PPG signals) on a sensor node in real-time to reduce data traffic while preserving signal fidelity and simultaneously, with very low power consumption. In some embodiments, an efficient embodiment of CS is applied to continuously compress the input signal on an embedded sensor node in a power efficient manner. This continuously compressed input signal is then wirelessly transmitted and reconstructed on a gateway device, in accordance with some embodiments. Various embodiments are described with reference to the input signal being a bio-signal (i.e., a signal associated with a living thing). However, the embodiments are not limited to such, and can be applied to sensing of any type of signal.

In some embodiments, an encoding scheme is described that uses a continuous sensing BPBD matrix along with symmetric padding of the input bio-signal to achieve high compression ratios for the bio-signals. In some embodiments, the encoding scheme is easily embeddable, highly power efficient and well suited for wearable applications. Furthermore, the BPBD encoding matrix can be used to recover the bio-signal in any basis in which the signal is sparse, in accordance with some embodiments.

Some embodiments describe a system architecture that involves a gateway logic (or a computing device) which initially sets the control parameters (e.g., compression ratio) for the compression algorithm and transmits this control information to the sensor node. In some embodiments, the sensor node encodes the bio-signal to a much lower dimension using a BPBD encoder to achieve high compression on the sensor node. In some embodiments, this compressed or encoded signal is then sent to another computing device (e.g., a gateway device) where the original signal is subsequently recovered with high fidelity using a linear optimization technique. In some embodiments, for ambulatory monitoring, the control parameters (e.g., compression ratio) may be updated periodically depending on the non-stationary status of the sampled signal. Other technical effects will be evident from the various embodiments.

In the following description, numerous details are discussed to provide a more thorough explanation of embodiments of the present disclosure. It will be apparent, however, to one skilled in the art, that embodiments of the present disclosure may be practiced without these specific details. In other instances, well-known structures and devices are shown in block diagram form, rather than in detail, in order to avoid obscuring embodiments of the present disclosure.

Note that in the corresponding drawings of the embodiments, signals are represented with lines. Some lines may be thicker, to indicate more constituent signal paths, and/or have arrows at one or more ends, to indicate primary information flow direction. Such indications are not intended to be limiting. Rather, the lines are used in connection with one or more exemplary embodiments to facilitate easier understanding of a circuit or a logical unit. Any represented signal, as dictated by design needs or preferences, may actually comprise one or more signals that may travel in either direction and may be implemented with any suitable type of signal scheme.

Throughout the specification, and in the claims, the term "connected" means a direct connection, such as electrical, mechanical, or magnetic connection between the things that are connected, without any intermediary devices. The term "coupled" means a direct or indirect connection, such as a direct electrical, mechanical, or magnetic connection between the things that are connected or an indirect connection, through one or more passive or active intermediary devices. The term "circuit" or "module" may refer to one or more passive and/or active components that are arranged to cooperate with one another to provide a desired function. The term "signal" may refer to at least one current signal, voltage signal, magnetic signal, or data/clock signal. The meaning of "a," "an," and "the" include plural references. The meaning of "in" includes "in" and "on."

The terms "substantially," "close," "approximately," "near," and "about," generally refer to being within +/−10% (unless otherwise specified) of a target value. Unless otherwise specified the use of the ordinal adjectives "first," "second," and "third," etc., to describe a common object, merely indicate that different instances of like objects are being referred to, and are not intended to imply that the objects so described must be in a given sequence, either temporally, spatially, in ranking or in any other manner.

For the purposes of the present disclosure, phrases "A and/or B" and "A or B" mean (A), (B), or (A and B). For the purposes of the present disclosure, the phrase "A, B, and/or C" means (A), (B), (C), (A and B), (A and C), (B and C), or (A, B and C).

For purposes of the embodiments, the transistors in various circuits, modules, and logic blocks are metal oxide semiconductor (MOS) transistors, which include drain, source, gate, and bulk terminals. The transistors also include Tri-Gate and FinFET transistors, Gate All Around Cylindrical Transistors, Tunneling FET (TFET), Square Wire, or Rectangular Ribbon Transistors or other devices implementing transistor functionality like carbon nano tubes or spintronic devices. MOSFET symmetrical source and drain terminals i.e., are identical terminals and are interchangeably used here. A TFET device, on the other hand, has asymmetric Source and Drain terminals. Those skilled in the art will appreciate that other transistors, for example, Bi-polar junction transistors—BJT PNP/NPN, BiCMOS, CMOS, eFET, etc., may be used without departing from the scope of the disclosure.

FIG. 1A illustrates ensemble 100 of wearable devices including one or more sensor nodes having apparatus for continuous CS of signals, according to some embodiments of the disclosure. In this example, ensemble 100 is on a person and his/her ride (here, a bicycle). However, the embodiments are not limited to such. Other scenarios of wearable devices and their usage may work with various embodiments.

For example, sensor nodes can be embedded into some other products (e.g., walls in a house, vehicles, clothes, body of a person, etc.) and can be controlled using a controller, gateway device, or computing device. The sensor node(s) of some embodiments can also be part of a wearable device. The term "wearable device" (or wearable computing device) generally refers to a device coupled to a person. For example, devices (such as sensors, cameras, speakers, microphones (mic), smartphones, smart watches, etc.) which are directly attached on a person or on the person's clothing are within the scope of wearable devices.

In some examples, wearable computing devices may be powered by a main power supply such as an AC/DC power outlet. In some examples, wearable computing devices may be powered by a battery. In some examples, wearable computing devices may be powered by a specialized external source based on Near Field Communication (NFC). The specialized external source may provide an electromagnetic field that may be harvested by circuitry at the wearable computing device. Another way to power the wearable computing device is electromagnetic field associated with wireless communication, for example, WLAN transmissions. WLAN transmissions use far field radio communications that have a far greater range to power a wearable computing device than NFC transmission. WLAN transmissions are commonly used for wireless communications with most types of terminal computing devices.

For example, the WLAN transmissions may be used in accordance with one or more WLAN standards based on Carrier Sense Multiple Access with Collision Detection (CSMA/CD) such as those promulgated by the Institute of Electrical Engineers (IEEE). These WLAN standards may be based on CSMA/CD wireless technologies such as Wi-Fi™ and may include Ethernet wireless standards (including progenies and variants) associated with the IEEE 802.11-2012 Standard for Information technology—Telecommunications and information exchange between systems—Local and metropolitan area networks—Specific requirements Part 11: WLAN Media Access Controller (MAC) and Physical Layer (PHY) Specifications, published March 2012, and/or later versions of this standard ("IEEE 802.11").

Continuing with the example of FIG. 1, ensemble 100 of wearable devices includes device 101 (e.g., camera, microphone, etc.) on a helmet, device 102 (e.g., blood pressure sensor, blood glucose sensor, temperature sensor, pulse sensor, etc.) on the person's arm, device 103 (e.g., a smart watch that can function as a terminal controller or a device to be controlled), device 104 (e.g., a smart phone and/or tablet in a pocket of the person's clothing), device 105 (e.g., pressure sensor to sense or measure pressure of a tire, or gas sensor to sense nitrogen air leaking from the tire), device 106 (e.g., an accelerometer to measure paddling speed), device 107 (e.g., another pressure sensor for the other tire). In some embodiments, ensemble 100 of wearable devices has the capability to communicate by wireless energy harvesting mechanisms or other types of wireless transmission mechanisms.

In some embodiments, device 102 comprises a sensor node which provides a power-efficient technique to deliver high compression of continuously sensed bio-signals (e.g., ECG/PPG signals) on the sensor node in real-time to reduce data traffic while preserving signal fidelity simultaneously, with very low power consumption. In some embodiments, an efficient method of CS is applied by the sensor node of device 102 to continuously compress the bio-signal on an embedded sensor node and wirelessly transmit the compressed bio-signal power efficiently. In some embodiments, a gateway device (e.g., a controller, a terminal device, a server in the cloud, etc.) reconstructs the originally sensed bio-signal from the received compressed bio-signal data. In some embodiments, an encoding scheme is described that uses BPBD matrix along with symmetric padding of the input signal to achieve high compression ratios for bio-signals (e.g., ECG and PPG signals).

In some embodiments, the sensor node of device 102 comprises a receiver to process an input bio-signal (e.g., ECG or PPG signal), an analog-to-digital converter (ADC) to convert the processed input signal to a digital stream, and logic which is operable to symmetrically pad on either ends of the digital stream with a portion of the digital stream to form a padded digital stream. In some embodiments, the sensor node of device 102 selects a part of the digital stream, transmits the selected part of the digital stream to another device (e.g., the gateway device), and receives one or more configuration parameters from the other device in response to the transmitted selected part of the digital stream. In some embodiments, the sensor node of device 102 selects a part of the raw bio-signal, transmits the selected part of raw bio-signal to another device (e.g., the gateway device), and receives one or more configuration parameters from the other device in response to the transmitted selected part of the raw bio-signal.

In some embodiments, prior to symmetrically padding on either ends of the digital stream, the sensor node of device 102 computes a number of elements to be padded using the one or more configuration parameters. In some embodiments, the number of elements determines the portion of the digital stream used for padding. In some embodiments, at least one of the one or more configuration parameters is dynamically (e.g., at any time) provided to the sensor node of device 102 by the other device (e.g., the gateway device). In some embodiments, at least one of the one or more configuration parameters is periodically (e.g., on regular intervals) provided to the sensor node of device 102 by the other device (e.g., the gateway device). In some embodiments, at least one of the one or more configuration parameters is a compression ratio.

In some embodiments, the sensor node of device 102 constructs an encoding matrix using the one or more configuration parameters, and then encodes the padded digital stream using the encoding matrix to generate compressed padded data. In some embodiments, the encoding matrix is a BPBD matrix. In some embodiments, the sensor node of device 102 transmits the compressed padded data to the other device for processing (e.g., decoding and reconstructing of the input signal).

In some embodiments, the sensor node of device 102 identifies types of at least two sensors including the sensor of the sensor node. For example, the sensor node of device 102 determines whether the sensing node is for receiving an ECG signal, or a particular type of a PPG signal. In some embodiments, the sensor node of device 102 aggregates information about the types of the at least two sensors and then transmits the aggregated information to the gateway device. In some embodiments, the sensor node of device 102 receives configuration parameters for each of the at least two sensors from the gateway device. As such, the encoding mechanisms of the at least two sensors are independently configured and optimized.

In some embodiments, instead of sending a selected portion of the digital stream to the gateway device to receive the optimized one or more configuration parameters, the sensor node of device 102 transmits a signal to the gateway device indicating a type of the sensor (e.g., ECG sensor, PPG sensor, etc.) or a type of the input signal (e.g., ECG signal, PPG signal, etc.). In some embodiments, the sensor node of device 102 receives one or more configuration parameters from the gateway device in response to the transmitted signal, where the one or more configuration parameters depend on the type of the sensor or the type of the input signal.

In some embodiments, the sensor comprises an antenna and a transmitter to transmit the encoded padded digital stream via the antenna to a computing device (or a gateway device) for processing (e.g., reconstruction of the originally sensed signal from the encoded signal). In some embodiments, the computing device dynamically or periodically instructs the sensor node to use a certain compression ratio according to the sensed signal and/or sensor node type.

Figure 1B:
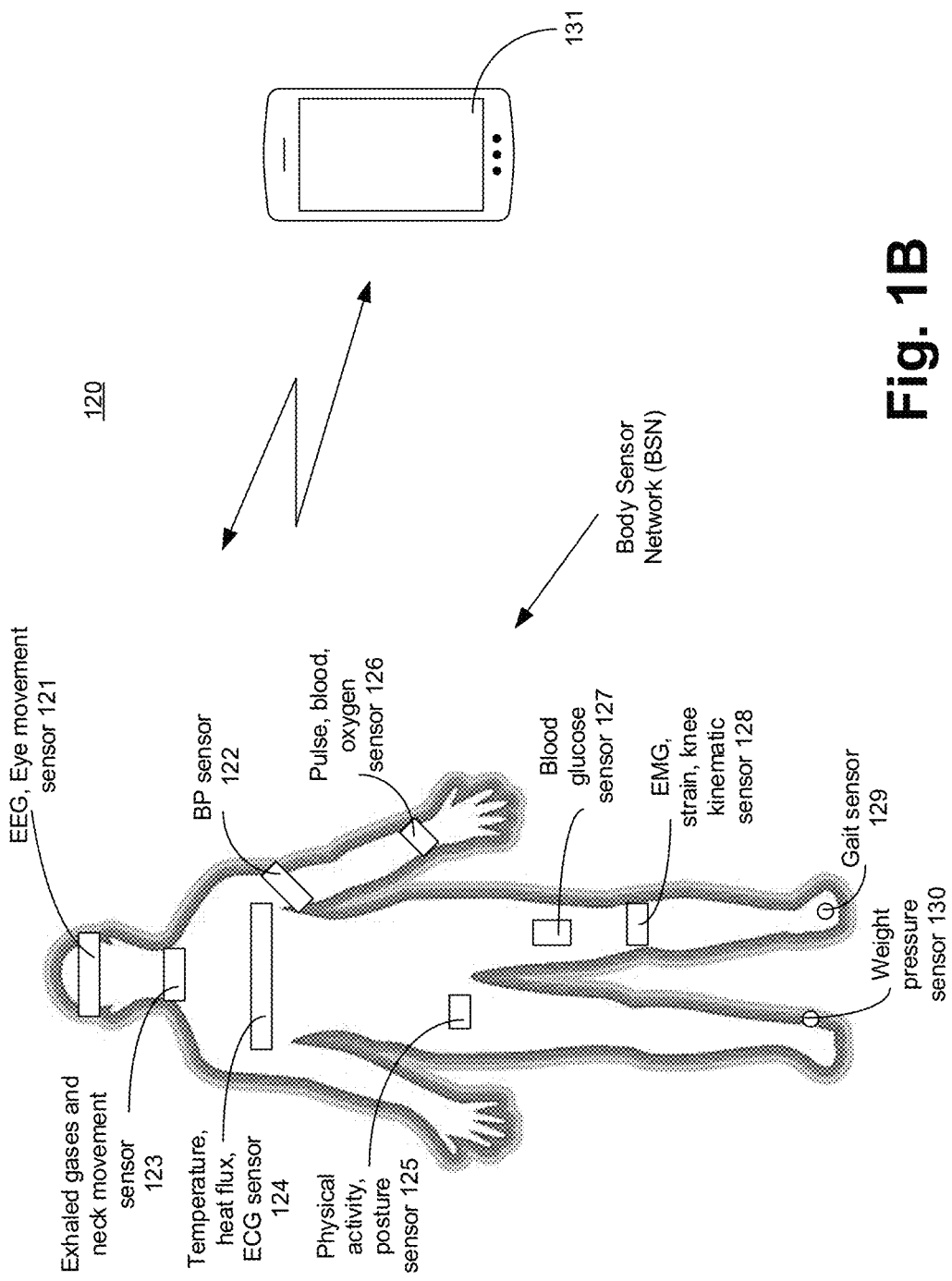
FIG. 1B illustrates a Body Sensor Network (BSN) with a plurality of sensor nodes having the apparatus for continuous CS of signals, according to some embodiments of the disclosure.

FIG. 1B illustrates system 120 with a BSN using a plurally of sensor nodes having apparatus for continuous CS of signals, according to some embodiments of the disclosure. It is pointed out that those elements of FIG. 1B having the same reference numbers (or names) as the elements of any other figure can operate or function in any manner similar to that described, but are not limited to such.

BSN is a wireless network of wearable computing devices. BSN devices may be embedded inside the body as implants or may be surface-mounted on the body in a fixed position. BSN may also include devices which humans can carry in different positions. For example, devices that can be carried in clothes pockets, by hand, or in various bags can be part of BSN. In this example embodiment, BSN comprises: EEG (electroencephalography) and/or eye movement sensor 121; blood pressure (BP) sensor 122; pulse, blood, exhaled gases and neck movement sensor 123, temperature, heat flux, and/or ECG sensor 124, physical activity posture sensor 125, pulse, blood, and/or oxygen sensor 126; blood glucose sensor 127; EMG (electromyography) strain, knee kinematic sensor 128; gait sensor 129, weight pressure sensor 130.

EEG sensor 121 can be used to measure voltage fluctuations resulting from ionic current within neurons of the brain. BP sensor 122 may include hardware to restrict blood flow and then measure the pressure caused by the redistricted blood flow. BP sensor 122 may use oscillometric detection mechanisms (e.g., using a piezoelectric pressure sensor) to infer systolic and diastolic pressures. ECG sensor 124 may use a number of electrodes (e.g., 10 to 12 electrodes) placed on various parts (e.g., limbs, chest, etc.) of the human's body to detect the heart's depolarization. EMG sensor 128 may detect electrical potential generated by cell muscles when these cells are electrically or neurologically activated. Gait sensor 129 is operable to gauge, for example, the pattern of movement of the limbs of humans. The sensors in the BSN are not meant to be a comprehensive list of sensors. Fewer or more sensors than illustrated may be used for forming the BSN.

A large amount of data is generated by each sensor node (e.g., sensors 121-130) in the BSN. Table 1 below illustrates sample data rates for different sensors in the BSN.

TABLE 1 sample rates from various sensors

| [Band | Sensors or signals | Number of channels 'n' (waveforms) | Sampling Rate (Hz) per channel | ADC Resolution | Throughput (Bytes/Sec) for 1 to 'n' channels | Total throughput for the band (Bytes/Sec) |
|---|---|---|---|---|---|---|
| Chest Band | ECG (bio-potential) | 1 to 3 | 300 | 16-bit | 600 to 1800 | 797 to 1997 (depends on number of ECG |
| | Respiration (piezoelectric) | 1 | 20 | 16-bit | 20 | |

TABLE 1-continued sample rates from various sensors

| [Band | Sensors or signals | Number of channels 'n' (waveforms) | Sampling Rate (Hz) per channel | ADC Resolution | Throughput (Bytes/Sec) for 1 to 'n' channels | Total throughput for the band (Bytes/Sec) |
|---|---|---|---|---|---|---|
| | GSR (conductance) | 1 | 20 | 16-bit | 20 | channels)] |
| | 3-Axes Acceleration (inertial) | 3 | 50 | 12-bit | 150 | |
| | Skin Temperature | 1 | 1 | 12-bit | 2 | |
| | Sweat Lactate (electrochemical) | 1 | 5 | 12-bit | 5 | |

In some embodiments, system 120 includes the BSN and a gateway device 131 (e.g., tablet computer, smartphone, laptop, computer in the cloud, etc.). In some embodiments, CS technique is used for real-time power efficient data compression of bio-signals in the BSN. In some embodiments, the encoding logic for CS resides on the sensor node (e.g., on sensors 121-130). In some embodiments, the encoding logic compresses the received bio-signal before transmission to gateway device 131. In some embodiments, gateway device 131 recovers the original bio-signal using a linear optimization algorithm.

Figure 2:
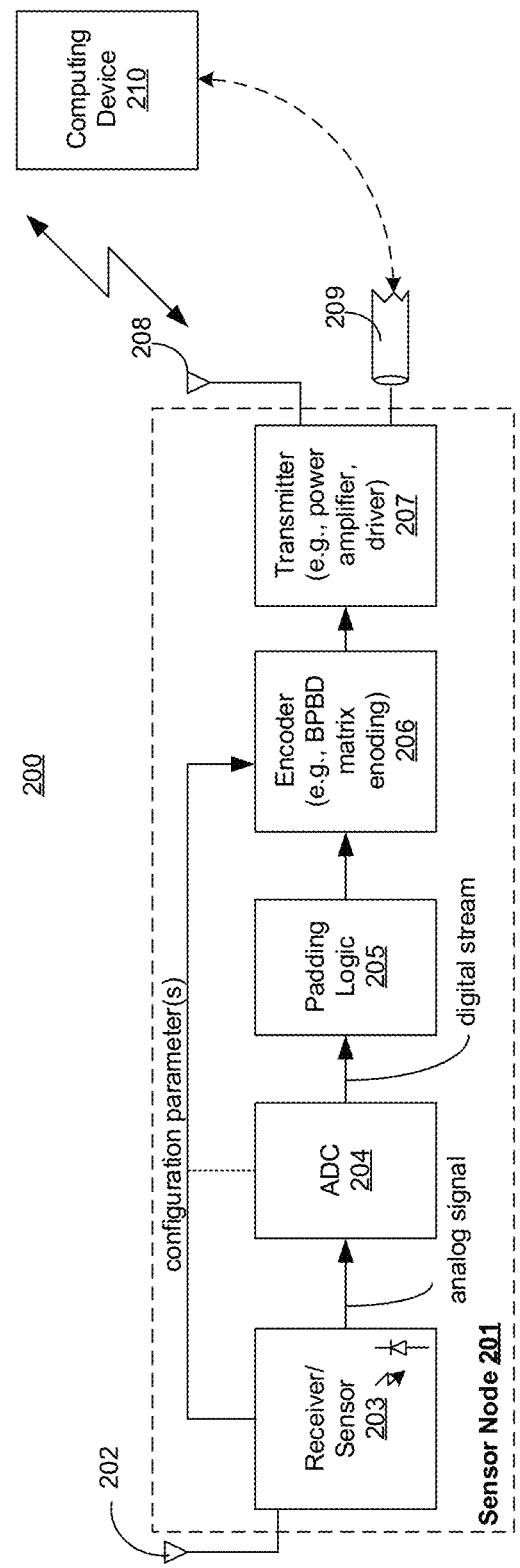
FIG. 2 illustrates a system with a sensor node having the apparatus for continuous CS of signals, according to some embodiments of the disclosure.

FIG. 2 illustrates system 200 with a sensor node having apparatus for continuous CS of signals, according to some embodiments of the disclosure. It is pointed out that those elements of FIG. 2 having the same reference numbers (or names) as the elements of any other figure can operate or function in any manner similar to that described, but are not limited to such.

In some embodiments, system 200 comprises sensor node 201 and computing device 210 (same as gateway device 131). In some embodiments, sensor node 201 comprises first antenna 202 (e.g., receiving antenna), Receiver/Sensor 203, ADC 204, Padding Logic 205, Encoder 206, Transmitter 207, second antenna 208 (transmitting antenna), and wired interface 209. In some embodiments, functions of first and second antennas 202 and 208, respectively, can be combined into a single antenna.

In some embodiments. Antenna(s) 202/208 are provided as part of sensor node 201 to communicate with other devices. In some embodiments, Antenna(s) 202/208 may comprise one or more directional or omnidirectional antennas, including monopole antennas, dipole antennas, loop antennas, patch antennas, microstrip antennas, coplanar wave antennas, or other types of antennas suitable for transmission of Radio Frequency (RF) signals. In some multiple-input multiple-output (MIMO) embodiments, Antenna(s) 202/208 are separated to take advantage of spatial diversity.

In some embodiments, Receiver/Sensor 203 includes a suitable sensing mechanism for sensing the bio-signal of interest. For example, Receiver/Sensor 203 includes a photodiode to detect light reflected from parts/organs of the human body and convert that detected light into current. In some embodiments, Receiver/Sensor 203 comprises an amplifier (such as a transimpedance amplifier) to convert the detected current into a voltage signal. In some embodiments, Receiver/Sensor 203 receives one or more configuration parameters (e.g., compression ratio) from Computing Device 210. In some embodiments, the output of Receiver/Sensor 203 is an analog signal (also referred to as raw data).

An analog signal is any continuous signal which is continuous in both time and amplitude such that the time varying feature (variable) of the signal is a representation of some other time varying quantity.

In some embodiments, the analog signal is converted into a digital stream by ADC 204. A digital signal or stream is a physical signal that is a representation of a sequence of discrete values (i.e., a quantified discrete-time signal), for example of an arbitrary bit stream. In some embodiments, the output of ADC 204 also includes digitized one or more configuration parameters which are then provided to Encoder 206. Any suitable ADC may be used to implement ADC 204. For example, ADC 204 is one of: direct-conversion ADC (for flash ADC), successive-approximation ADC, ramp-compare ADC. Wilkinson ADC, integrating ADC, delta-encoded ADC or counter-ramp, pipeline ADC (also called subranging quantizer), sigma-delta ADC (also known as a delta-sigma ADC), time-interleaved ADC, ADC with intermediate FM stage, or time-stretch ADC.

In some embodiments, the digital stream is receive by Padding Logic 205 that manipulates the digital stream to provide a padded digital stream for Encoder 206. In some embodiments, Padding Logic 205 is operable to symmetrically pad on either ends of the digital stream with a portion of the digital stream to form the padded digital stream. The portion of the digital stream can be, for example, a predetermined or programmable number of initial or ending bits of the digital stream. In some embodiments, prior to symmetrically padding on either ends of the digital stream, the sensor node 201 computes a number of elements to be padded using the one or more configuration parameters. In some embodiments, the number of elements determines the portion of the digital stream.

Figure 3:
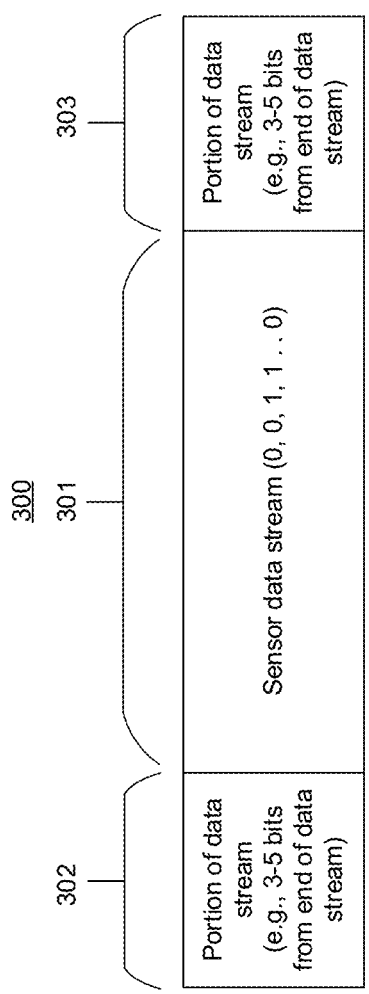
FIG. 3 illustrates a padded digital stream, according to some embodiments of the disclosure.

FIG. 3 illustrates a padded digital stream 300, according to some embodiments of the disclosure. In some embodiments, digital stream 301 (e.g., sensor data stream having bits of zeros and ones) is padded by portions 302 and 303 (e.g., 3-5 bits from the digital stream 301) on either ends of digital stream 301. Referring back to FIG. 2, in some embodiments, sensor node 201 selects a part of the digital stream, transmits the selected part of the digital stream to Computing Device 210, and receives one or more configuration parameters from Computing Device 210 in response to the transmitted selected part of the digital stream.

In some embodiments, Encoder 206 receives the padded digital stream and compresses or encodes the padded digital stream. In some embodiments, Encoder 206 constructs an encoding matrix using the one or more configuration parameters, and then encodes the padded digital stream using the encoding matrix to generate the compressed padded data. In some embodiments, the encoding matrix meets multiple stringent constraints simultaneously.

For example, the encoding matrix meets the criteria of: being embeddable in compact form, delivering high compression performance with low reconstruction error, performing well on important bio-signals such as ECG and PPG in cases in which they are known to be sparse, and providing highly power efficient battery life. In some embodiments, the encoding matrix is a BPBD matrix.

Figure 4:
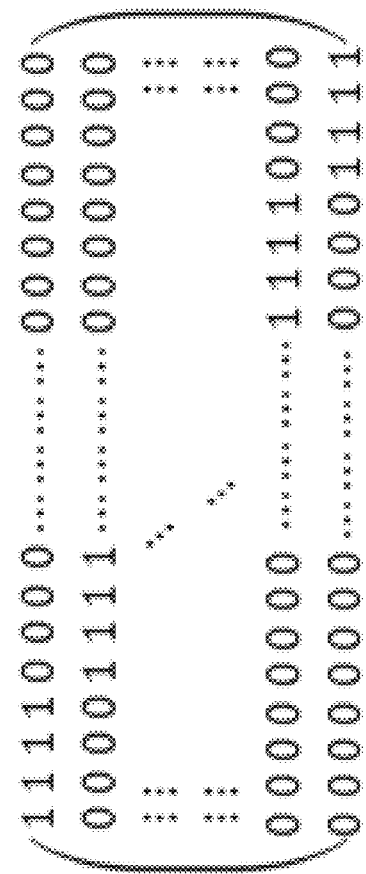
FIG. 4 illustrates a Binary Permuted Block Diagonal (BPBD) matrix used by the apparatus for continuous CS of signals, according to some embodiments of the disclosure.

FIG. 4 illustrates a sample BPBD matrix 400 used by Encoder 206 for continuous CS of signals, according to some embodiments of the disclosure. BPBD matrix 400 comprises of a sub-matrix of 1's which is arranged as a block along the diagonal with the off-diagonal elements set to zero. The number of elements or size of the sub-matrix in BPBD matrix 400 is N/M, where 'N' is a number of columns and 'M' is a number of rows. In some embodiments, 'N' is the number of samples in the window. As such, the size of the sub-matrix is essentially the compression ratio.

In some embodiments, BPBD matrix 400 is constructed using a target compression ratio control setting received from Computing Device 210. Ordinarily, a feasible compression point using the traditional BPBD method is one where the number of samples in a window is exactly divisible by the sub-matrix size or compression ratio. This implies that merely a discontinuous set of compression ratios are feasible for a fixed sampling window size (i.e., the size in terms of number of bits of the digital stream from ADC 204).

In some embodiments, a refined method is used that enables any desired integer compression ratio (without discontinuities) using BPBD matrix 400. In some embodiments, samples are padded by Padding Logic 205 to the input of the digital stream from the last element of the signal window (i.e., symmetric padding) to match the dimensions of BPBD matrix 400 for each compression ratio enabling the matrix inner product. In other embodiments other types of encoding matrices may be used that meet the constraints discussed here.

Referring back to FIG. 2, in some embodiments, Transmitter 207 transmits the compressed padded data to Computing Device 210 for processing (e.g., decoding and reconstructing of the input signal). Transmitter 207 may use any known transmitting scheme. For example Transmitter 207 uses WLAN transmissions in accordance with one or more WLAN standards based on CSMA/CD such as those promulgated by the IEEE to transmit the compressed data to Computing Device 210. These WLAN standards may be based on CSMA/CD wireless technologies such as Wi-Fi™ and may include Ethernet wireless standards (including progenies and variants) associated with the IEEE 802.11. In some embodiments. Transmitter 207 may use Long Term Evolution (LTE) compliant transmission mechanisms.

Any suitable low power transmitter may be used for implementing Transmitter 207 (e.g., a transmitter having low power amplifier driver). In some embodiments, Transmitter 207 converts the compressed padded data to an analog radio frequency (RF) signal which is then transmitted by antenna 208 to Computing Device 210. In other embodiments, other forms of wireless transmissions may be used by Transmitter 207.

In some embodiments, Transmitter 207 includes a DAC (not shown) to convert the compressed digital data into analog signal for transmission. In some embodiments, the DAC is a pulse-width modulator (PCM). In some embodiments, the DAC is an oversampling DAC or interpolating DAC such as sigma-delta DAC. In other embodiments, other types of DAC may be used. For example, the DAC of Transmitter 207 is one of switched resistor DAC, switched current source DAC, switched capacitor DAC, R-2R binary weighted DAC, Successive-Approximation or Cyclic DAC, thermometer-coded DAC, etc. The output the DAC is an analog signal which is amplified and then transmitted via wired channel 209 to antenna 208 to Computing Device 210, according to some embodiments.

In some embodiments, Computing Device 210 is any gateway device (e.g., smartphone, tablet, laptop, computing resource in the cloud, etc.) which is operable to process large amount of data. In some embodiments, Computing Device 210 includes a receiver to receive the compressed data from sensor node 201. In some embodiments, Computing Device 210 includes a decoder to decode the encoded compressed data to recover the signal sensed over time by Receiver/Sensor 203.

Figure 5:
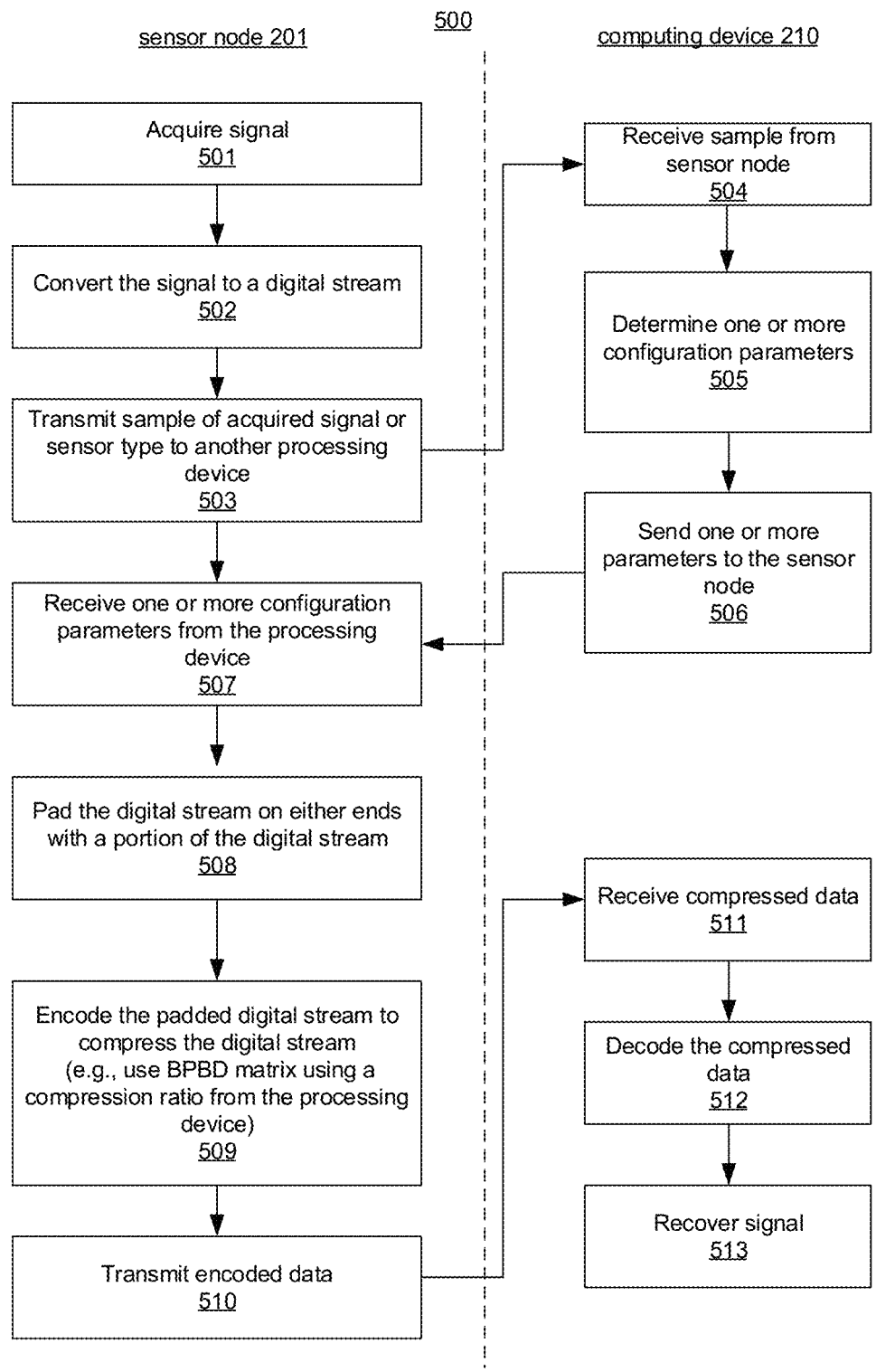
FIG. 5 illustrates a flowchart of a method for continuous CS of signals, according to some embodiments of the disclosure.

FIG. 5 illustrates flowchart 500 of a method for continuous CS of signals, according to some embodiments of the disclosure. It is pointed out that those elements of FIG. 5 having the same reference numbers (or names) as the elements of any other figure can operate or function in any manner similar to that described, but are not limited to such.

Although the blocks in the flowchart with reference to FIG. 5 are shown in a particular order, the order of the actions can be modified. Thus, the illustrated embodiments can be performed in a different order, and some actions/blocks may be performed in parallel. Some of the blocks and/or operations listed in FIG. 5 are optional in accordance with certain embodiments. The numbering of the blocks presented is for the sake of clarity and is not intended to prescribe an order of operations in which the various blocks must occur. Additionally, operations from the various flows may be utilized in a variety of combinations.

At block 501, Receiver/Sensor 203 acquires the bio-signal via antenna 202 or wired means (e.g., a cable attached to the chest or a person). In some embodiments, the bio-signal may be a current, light, magnetic signal, etc., and is converted into an analog signal (e.g., an analog voltage signal). At block 502, ADC 204 converts the analog signal to a digital stream.

At block 503, a portion or sample of the digital stream is provided to Transmitter 207 to transmit that portion or sample to another processing device (i.e., Computing Device 210 via antenna 208 or wired means 209). In some embodiments, a sensor type (e.g., whether sensor node 201 is an ECG sensor, a BP sensor, etc.) is sent to Computing Device 210 from sensor node 201. At block 504, Computing Device 210 receives the sample of the acquired signal or type of the sensor. At block 505, Computing Device 210 determines one or more configuration parameters (e.g., compression ratio) according to the received sample and/or type of sensor. At block 506, Computing Device sends the one or more configuration parameters (e.g., compression ratio) to sensor node 201. In some embodiments, the analog signal is provided to Transmitter 207 to transmit to Computing Device 210. In one such embodiment, Computing Device 210 uses the analog signal to determine the one or more configuration parameters for sensor node 201.

In some embodiments, Computing Device 210 dynamically sets the compression ratio for the compression algorithm (that is implemented by Encoder 206) and trades off reconstruction loss percentage against accuracy of features extracted from recovered signal. In some embodiments, Computing Device 210 periodically transmits this target compression ratio setting to sensor node 201.

At block 507, sensor node 201 receives the one or more configuration parameters. For example, sensor node 201 receives the one or more configuration parameters via antenna 202. At block 508, Padding Logic 205 pads the digital stream on both ends with a portion of the digital stream. In some embodiments, Padding Logic 205 symmetrically pads the digital stream on both ends with a predetermined bit pattern. At block 509, Encoder 206 applies this target compression ratio and compresses the digital stream representing the bio-signal to a much lower dimension using a CS encoding matrix. In some embodiments, the CS encoding matrix is used to achieve power-efficient compression on sensor node 201. In some embodiments, at block 509, Encoder 206 constructs an encoding matrix using the one or more configuration parameters, and then encodes the padded digital stream using the encoding matrix to generate compressed padded data. In some embodiments, the encoding matrix is a BPBD matrix.

At block 510, Transmitter 207 of sensor node 201 transmits the compressed padded data to Computing Device 210 (e.g., for decoding and reconstructing of the input signal). At block 511, Computing Device 210 receives the compressed data. At block 512, Computing Device 210 decodes the received compressed data. At block 513, Computing Device 210 subsequently recovers the original bio-signal with high fidelity using a linear optimization technique (e.g., an L1-Norm based optimizer).

In some embodiments, the encoding matrix for the bio-signals (e.g., ECG and PPG signals) is embeddable in sensor node 201. As such, memory and computational power requirements on sensor node 201 are reduced, yet providing fast and accurate reconstruction of the ECG and PPG signal on Computing Device 210.

Figure 6:
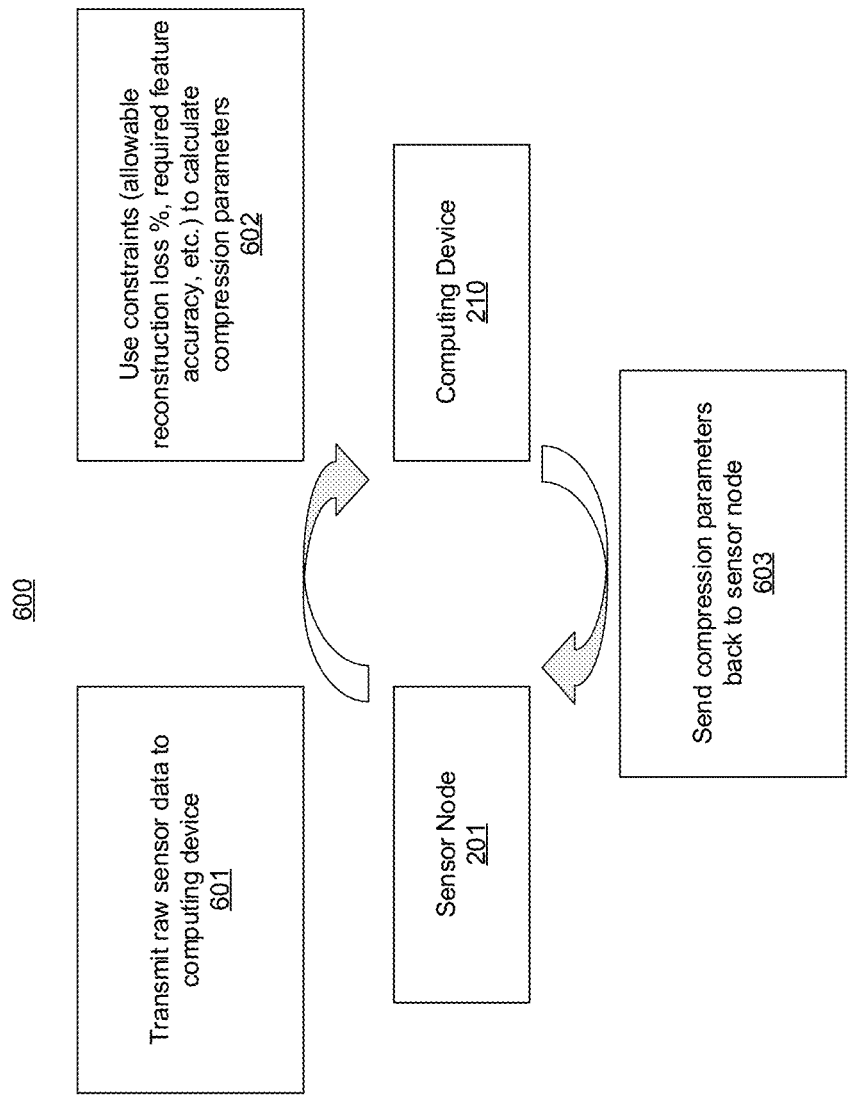
FIG. 6 illustrates a flowchart of a method for dynamic and/or periodic update of one or more configuration parameters for continuous CS of signals, according to some embodiments of the disclosure.

FIG. 6 illustrates flowchart 600 of a method for dynamic and/or periodic update of one or more configuration parameters for continuous CS of signals, according to some embodiments of the disclosure. It is pointed out that those elements of FIG. 6 having the same reference numbers (or names) as the elements of any other figure can operate or function in any manner similar to that described, but are not limited to such.

Although the blocks in the flowchart with reference to FIG. 6 are shown in a particular order, the order of the actions can be modified. Thus, the illustrated embodiments can be performed in a different order, and some actions/blocks may be performed in parallel. Some of the blocks and/or operations listed in FIG. 6 are optional in accordance with certain embodiments. The numbering of the blocks presented is for the sake of clarity and is not intended to prescribe an order of operations in which the various blocks must occur. Additionally, operations from the various flows may be utilized in a variety of combinations.

In some embodiments, in continuous ambulatory monitoring where the sampled signal is likely to show significant variability in morphology, noise, signal quality, etc., the compression ratio is periodically updated and transmitted by Computing Device 210 to sensor node 201 as input to Encoder 206. This enables tuning the compression logic in real-time to meet application-dependent quality constraints, in accordance with some embodiments. Flowchart 600 describes one such method for dynamic and/or periodic update of one or more configuration parameters for continuous CS of signals, in accordance with some embodiments.

At block 601, raw sensor data (e.g., a portion of unpadded digital stream) is transmitted by Transmitter 207 of sensor node 201 to Computing Device 210. At block 602, Computing Device 210 uses constraints such as allowable reconstruction loss percentage, required accuracy, etc. to calculate compression parameters. In some embodiments, a higher granular compression ratio is desired to accurately cover the signals received from the BSN. In some embodiments, Computing Device 210 determines the compression ratio by balancing competing parameters such as power consumption requirements of the sensor node and the reconstruction loss.

For example, if the compression ratio (e.g., 2) selected is too low, sensor node 201 will dissipate more transmitter/radio power. Likewise, if the compression ratio (e.g., 32) selected by Computing Device 210 is too high, then the reconstruction loss may be unacceptable. In some embodiments, Computing Device 210 finds the right balance of competing criteria for each sensor node in the BSN. At block 603, Computing Device 210 sends the compression parameters back to sensor node 201. This process can be performed periodically or dynamically to reduce the reconstruction loss percentage and/or balance power usage at sensor node 201.

Figure 7:
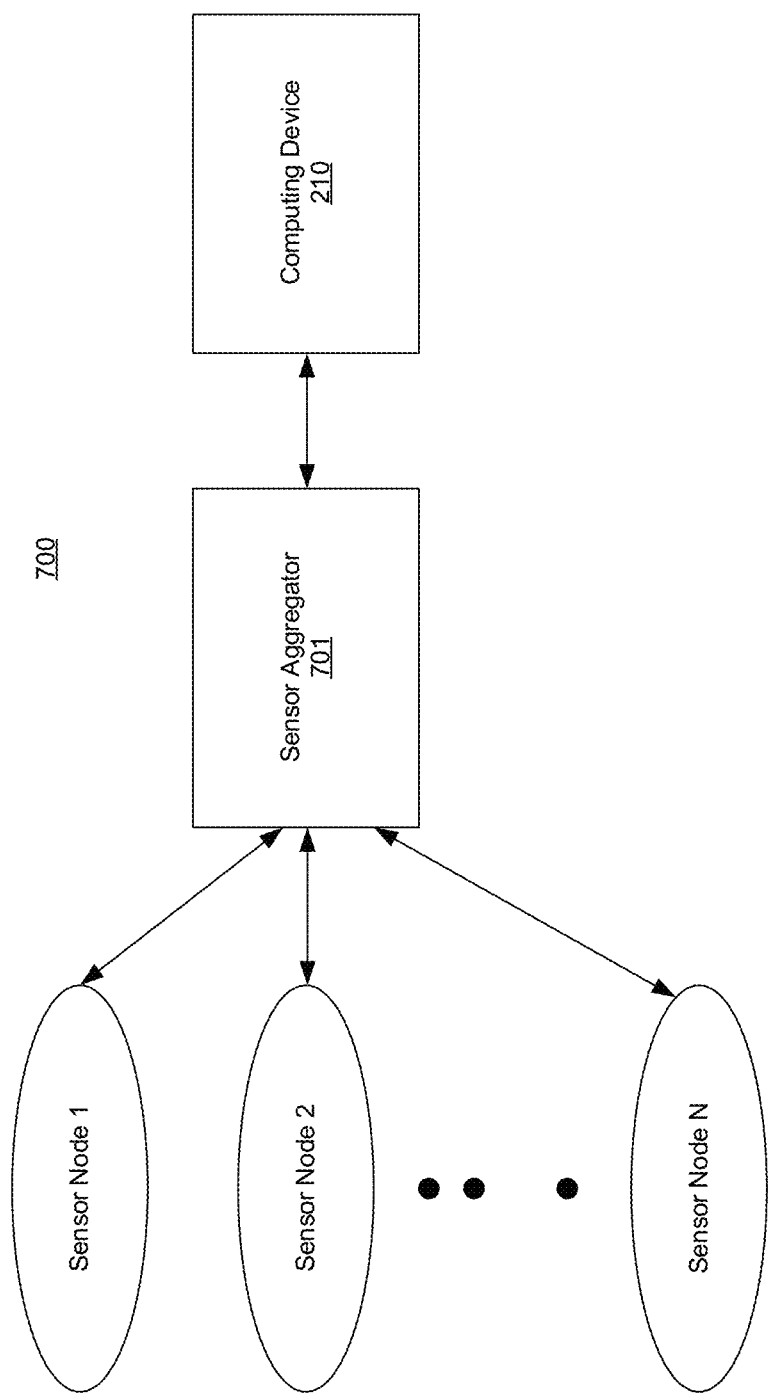
FIG. 7 illustrates a system for aggregating sensor data for efficient continuous CS of signals, according to some embodiments of the disclosure.

FIG. 7 illustrates system 700 for aggregating sensor data, according to some embodiments of the disclosure. It is pointed out that those elements of FIG. 7 having the same reference numbers names) as the elements of any other figure can operate or function in any manner similar to that described, but are not limited to such.

In some embodiments, system 700 comprises a plurality of sensor nodes (e.g., Sensor Node 1 to 'N,' where 'N' is an integer greater than 1), Sensor Aggregator 701, and Computing Device 210. In some embodiments, Sensor Aggregator 701 acts as an intermediary node or device that collects the compressed data from the plurality of sensor nodes and sends that data to Computing Device 210 for processing. In some embodiments, Sensor Aggregator 701 also provides (periodically or dynamically) one or more configuration parameters to the plurality of sensor nodes from Computing Device 210. In some embodiments, Sensor Aggregator 701 is in closer proximity to the plurality of sensor nodes than the plurality of sensor nodes are from Computing Device 210. As such, complexity and power consumption of sensor nodes can be further reduced because the sensor nodes do not have to communicate long distances.

FIGS. 8-12 illustrate various plots, some of which show the technical effects of various embodiments compared to traditional compression techniques. Results of BPBD-CS modeling and embedded power measurements for ECG and PPG are illustrated. It is pointed out that those elements of FIGS. 8-12 having the same reference numbers (or names) as the elements of any other figure can operate or function in any manner similar to that described, but are not limited to such.

The various embodiments provide higher compression, accuracy, and lower power dissipation compared to known compression techniques. Some embodiments are assessed under two different constraints used in signal reconstruction: Percentage Root-Mean-Square Difference (PRD) and heart-rate accuracy. Here, PRD measures the accuracy to reconstruct the entire signal supported by the digital stream (i.e., window). PRD can be expressed as:

$$PRD = \sqrt{\frac{\sum_{n=1}^{N}(x1[n] - x2[n])^2}{\sum_{n=1}^{N}(x1[n])^2}} \times 100$$

where "x1" is the original signal, "x2" is the reconstructed signal, and 'N' is the length (i.e., dimensionality) of both the signals (i.e., "x1" and "x2" signals).

Here, heart-rate accuracy refers to differences in beat-rate calculated from the recovered signal and compared to the beat rate calculated from the original uncompressed signal (i.e., measure of accuracy in reconstructing only relevant signal features from the digital stream). This approach of assessing signal reconstruction under the two different constraints (i.e., PRD and heart-rate) allows a designer to decide which constraint to use and hence set the compression parameters. Some embodiments apply the constraint of feature accuracy to push the compression ratio far beyond that obtained to meet the PRD constraint.

The term "feature accuracy" generally refers to using the feature value extracted from the uncompressed original raw signal as reference standard. For example, if beat rate of raw ECG is 72 bpm and that extracted from the reconstructed signal is say, 75 bpm then the feature error is 3 bpm and the feature accuracy is approximately 96%.

Table 2 shows that the BPBD matrix of some embodiments has excellent incoherency for CS with respect to the Fourier basis.

TABLE 2

| [Compression ratio CR (N/M) | BPBD matrix size (M × N) | Window size of input signal after padding (N) | Lower limit (1/√N) | Coherence (1/√N, 1) |
|---|---|---|---|---|
| 2 | 256 × 512 | 512 | 0.0442 | 0.0626 |
| 5 | 103 × 515 | 515 | 0.0441 | 0.0990 |
| 10 | 52 × 520 | 520 | 0.0439 | 0.1399 |
| 15 | 35 × 525 | 525 | 0.0436 | 0.1713 |
| 20 | 26 × 520 | 520 | 0.0439 | 0.1995 |
| 25 | 21 × 525 | 525 | 0.0436 | 0.2228] |

The term "incoherence" generally refers to the largest correlation between 'Φ' (sensing matrix) and 'Ψ' (sparse basis) which is the inverse of the Discrete Fourier Transform (DFT) matrix, and expressed as:

$$\mu(\Phi, \Psi) = \max_{1 \leq i, j \leq N} |\langle \Phi_i, \Psi_j \rangle|$$

where "$\Phi_i$" are rows of 'Φ,' "$\Psi_j$" are columns of 'Ψ,' 'Φ' is the size M×N of the BPBD matrix, 'Ψ' is the size N×N of the sparse basis, and 'N' is the padded window size obtained after samples are artificially added to the original input window by symmetric padding, in accordance with some embodiments.

In some embodiments, the specific number of samples added to the digital stream is given by the difference of the original window size and the nearest multiple of the CR greater than the original window size. For example, if the CR is 5 as in Table 2, for an original window size of 512 samples, the number of padded elements is 3 and the BPBD matrix size is 103×515 and the size of the sparse basis 'Ψ' is 515×515.

Figure 8A:
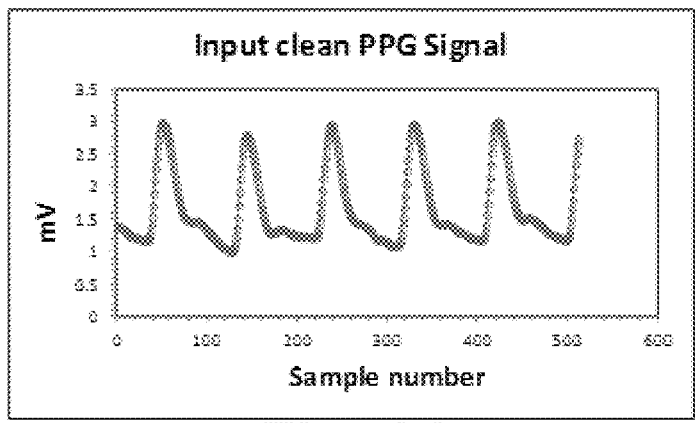
FIG. 8A illustrates a plot showing a clean input Photoplethysmogram (PPG) signal.

FIG. 8A illustrates plot 800 showing a clean input PPG signal. Here, x-axis is sample number and y-axis is the amplitude of the PPG signal in millivolts (mV) (e.g., analog output of Receiver/Sensor 203). In this example, the input clean PPG signal has 512 samples.

Figure 8B:
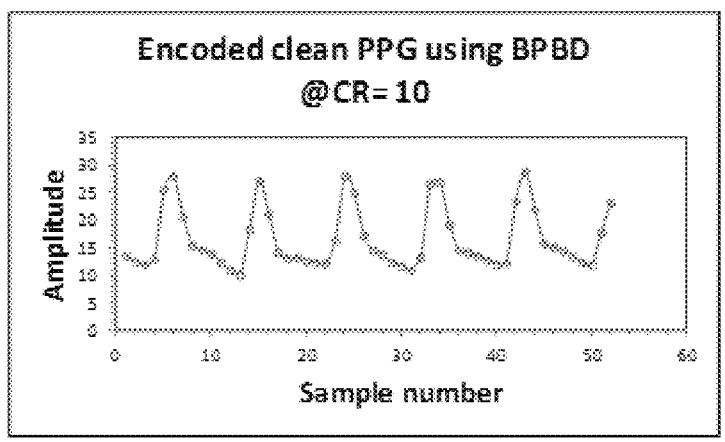
FIG. 8B illustrates a plot showing the effect of encoding the clean PPG signal of FIG. 8A by a sensor node according to some embodiments of the disclosure.

FIG. 8B illustrates plot 820 showing the effect of encoding by sensor node 201 the clear PPG signal of FIG. 8A, according to some embodiments of the disclosure. Here, x-axis is sample number and y-axis is the magnitude of amplitude of the encoded PPG signal (e.g., output of Encoder 206 using BPBD encoding matrix at CR of 10). In this example, encoding the padded digital stream (obtained from the clean PPG signal) with BPBD encoding matrix at CR of 10 reduces the dimensionality to 52. samples (from 512 samples). In some embodiments, the size of the encoding sub-matrix is determined dynamically at Computing Device 210 using an initial sample set by constraints such as target signal recovery quality and feature accuracy as required by the application.

Figure 8C:
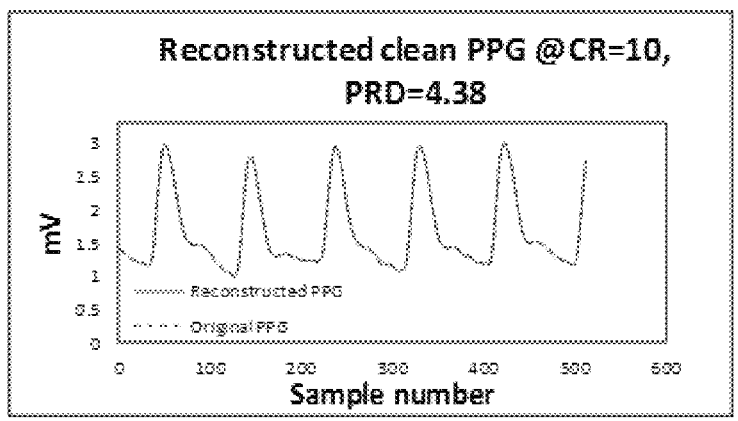
FIG. 8C illustrates a plot showing the reconstruction of the PPG signal by a computing device, according to some embodiments of the disclosure.

FIG. 8C illustrates plot 830 showing reconstruction of the PPG signal by Computing Device 210, according to some embodiments of the disclosure. Here, x-axis is sample number and y-axis is the amplitude of the PPG signal in mV.

Figure 9A:
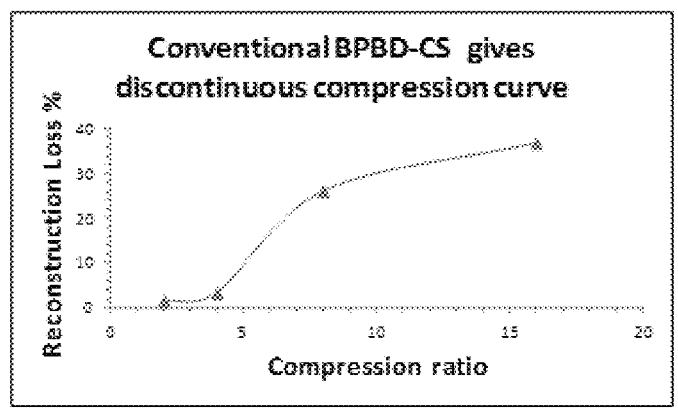
FIG. 9A illustrates a plot showing the compression of data using a typical BPBD based encoding matrix that provides a discontinuous compression curve.
Figure 9B:
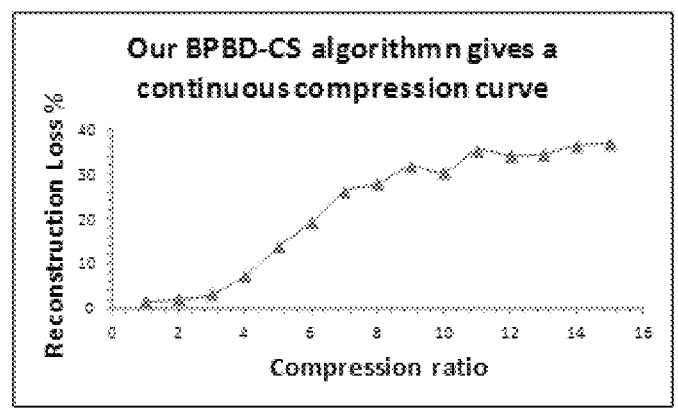
FIG. 9B illustrates a plot showing the compression of data using the BPBD based encoding matrix that provides a continuous compression curve, according to some embodiments.

FIG. 9A illustrates plot 900 showing the compression of data using a typical BPBD based encoding matrix that results in a discontinuous compression curve. FIG. 9B illustrates plot 920 showing the compression of data using BPBD based encoding matrix that provides a continuous compression curve, according to some embodiments.

Figure 10A:
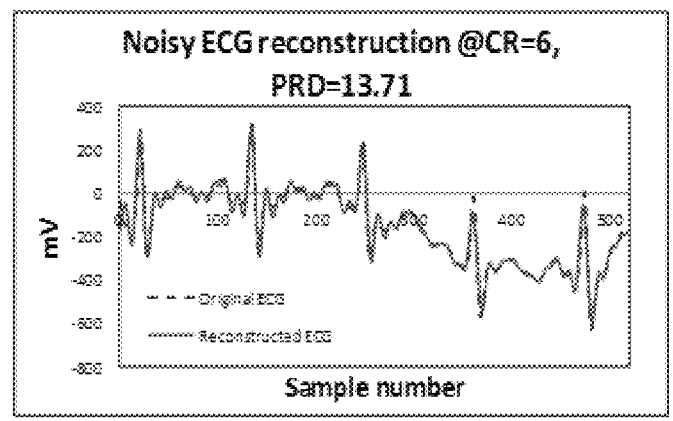
FIGS. 10A-B illustrate plots showing noisy reconstruction of signals using Percentage Root Mean Square Difference (PRD) with two different compression ratios.
Figure 10B:
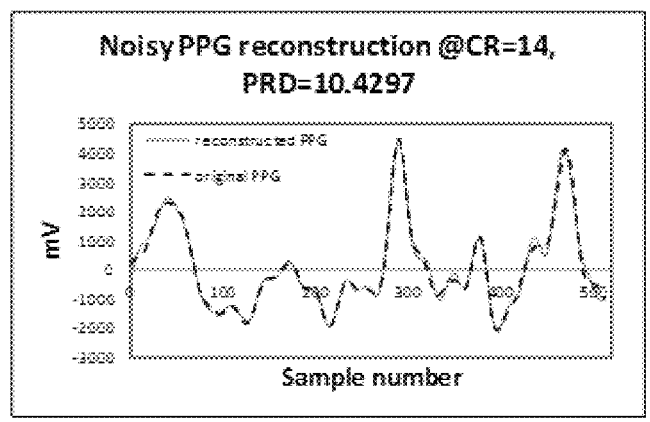

FIGS. 10A-B illustrate plots 1000 and 1020 showing noisy reconstruction of signals using PRD with two different compression ratios, in accordance with some embodiments.

Various embodiments work well even for a noisy ECG signal with baseline wander (as shown in FIG. 10A) and a noisy PPG signal with motion artefacts (as shown in FIG. 10B). As such, the BPBD encoding scheme of various embodiments can be used to power-efficiently transmit either a clean or noisy ECG or PPG signal to Computing Device 210 and reconstruct it there (where there is relatively abundant compute power as well as energy). As such, continuous monitoring is enabled by taking advantage of the asymmetry in computational power between sensor node 201 and Computing Device 210.

In some embodiments, the extent of achievable compression depends on the specific constraints set by the application. Table 3 illustrates an example of the impact of PRD and beat-rate accuracy constraints on the maximum achievable CR.

TABLE 3

| [Signal | Constraint | Max CR achievable | Remarks |
|---|---|---|---|
| ECG | PRD = 14% | 6 | |
| ECG | accurate beat rate | 11 | Accurate beat rate can be extracted even with poor recovered signal quality (PRD = 40.05%) |
| PPG | PRD = 10% | 14 | |
| PPG | accurate beat rate | 23 | Accurate beat rate can be extracted even with poor recovered signal quality (PRD = 18.19%)] |

Figure 11A:
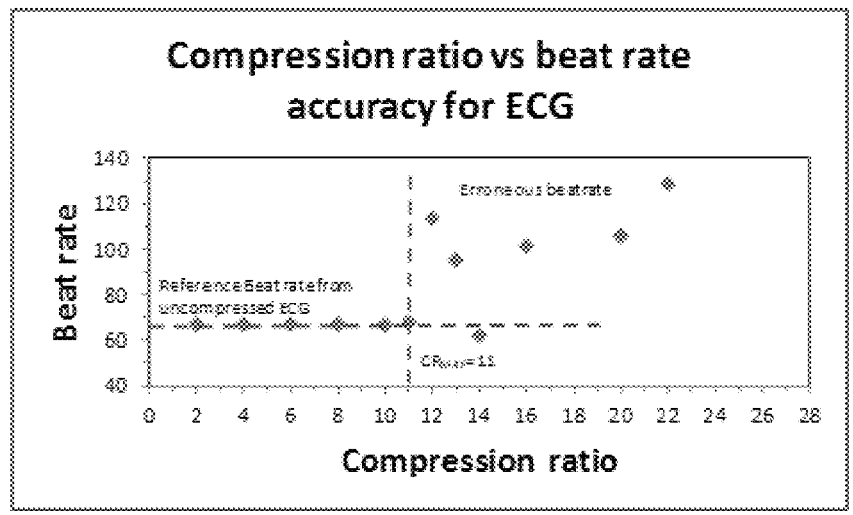
FIGS. 11A-B illustrate plots showing effects of compression ratio on beat rate accuracy for Electrocardiogram (ECG) and PPG signals, according to some embodiments of the disclosure.
Figure 11B:
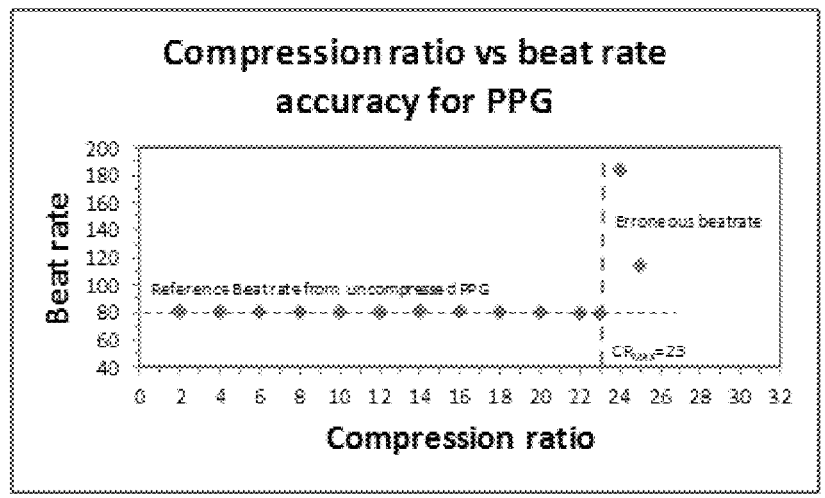

FIGS. 11A-B illustrate plots 1100 and 1120 showing effects of CR on beat rate accuracy for ECG and PPG signals, according to some embodiments of the disclosure. Here, x-axis is compression ratio and y-axis is beat rate. For a PRD of approximately 10%, a CR=14 can be achieved for PPG. In some cases, where only the beat rate is of interest and the overall signal quality is of secondary concern, a CR=23 can be achieved for the same PPG signal cutting data transmission traffic by a factor of 23. With some embodiments, even when the reconstructed signal quality is poor (PRD is approximately 20%), an extract accurate beat-rate can still be extracted.

Figure 12A:
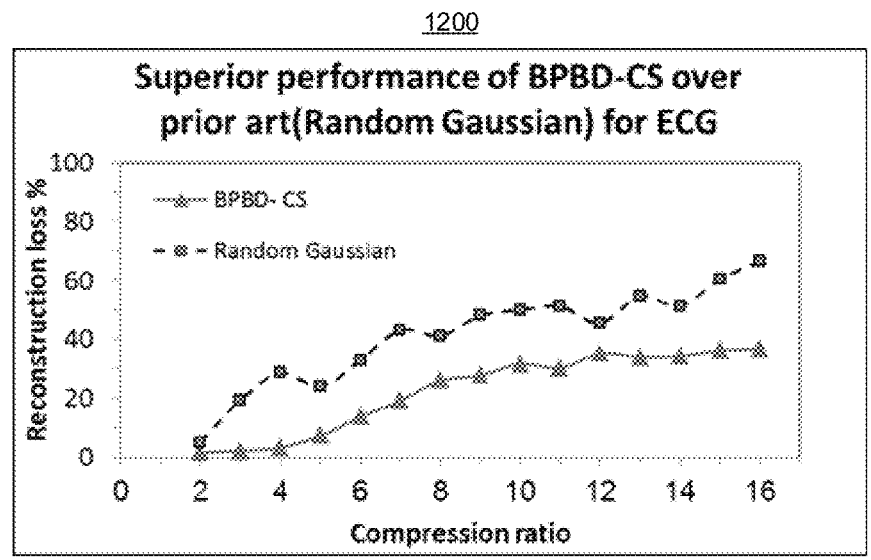
FIGS. 12A-B illustrate plots showing improvement, over prior art techniques, in reconstruction of the ECG and PPG signals using BPBD encoding matrix generated by the apparatus and/or methods of various embodiments.
Figure 12B:
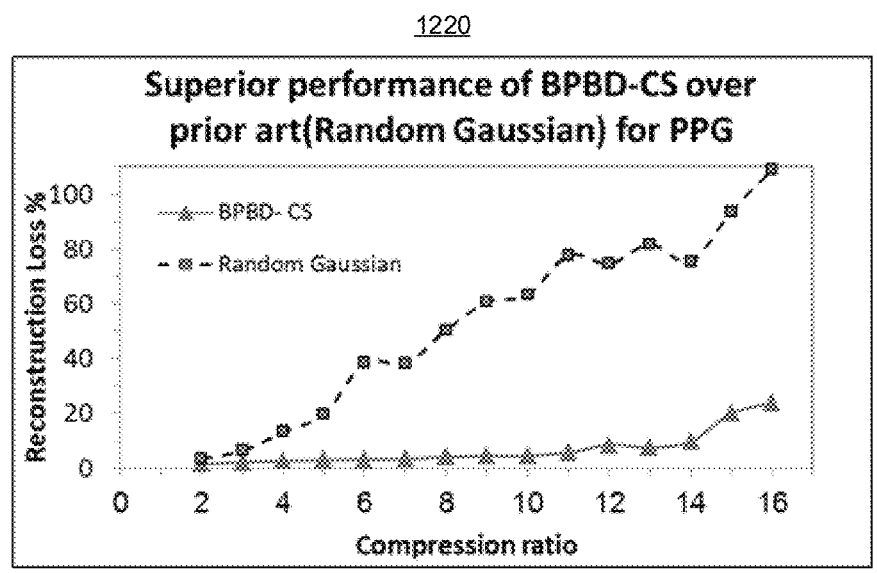

FIGS. 12A-B illustrate plots showing improvement, over prior art techniques, in reconstruction of the ECG and PPG signals using BPBD encoding matrix generated by the apparatus and/or methods of various embodiments.

Here, x-axis is CR and y-axis is percentage of reconstruction loss. Plots 1200 and 1220 show that the padded BPBD-CS scheme of various embodiments is superior to prior art techniques such as Random Gaussian based CS and DWT. Although the random Gaussian CS is not easily embeddable, it can deliver a continuous compression curve which we also achieve using BPBD-CS through data padding. Plots 1200 and 1220 show that the BPBD-CS scheme of various embodiments outperforms the random Gaussian algorithm across a range of compression ratios for ECG and PPG signals (i.e., for the same compression ratio, various embodiments achieve a much lower reconstruction loss %).

The BPBD-CS scheme of various embodiments is also more power efficient for the same reconstruction quality using the CS implementation relative to a state of the art DWT compression algorithm. In some embodiments, the embedded BPBD scheme is approximately 100× faster than the DWT scheme with energy consumption less than 1% of that of the DWT scheme at the same reconstruction loss.

Table 4 and Table 5 illustrate negligible power consumption for BPBD-CS of various embodiments over the DWT scheme for ECG and PPG signals.

TABLE 4

| [Reconstruction loss %] | BPBD | | | DWT | | |
|---|---|---|---|---|---|---|
| | CR | Time(ms) | Energy($\mu$J) | CR | Time(ms) | Energy($\mu$J) |
| 1.508 | 2 | 0.52 | 1.131 | 3.122 | 22 | 585.54 |
| 2.183 | 3 | 0.5 | 1.067 | 3.325 | 23 | 611.33 |
| 3.259 | 4 | 0.5 | 1.047 | 3.556 | 23 | 737.79 |
| 7.397 | 5 | 0.49 | 1.026 | 5.753 | 11 | 360.7 |
| 13.869 | 6 | 0.48 | 1.023 | 6.649 | 11 | 361.49] |

TABLE 5

| [Reconstruction loss %] | BPBD | | | DWT | | |
|---|---|---|---|---|---|---|
| | CR | Time(ms) | Energy($\mu$J) | CR | Time(ms) | Energy($\mu$J) |
| 0.116 | 2 | 0.62 | 1.320 | 2.485 | 21 | 666.85 |
| 0.211 | 3 | 0.61 | 1.252 | 3.241 | 22 | 708.91 |
| 0.271 | 4 | 0.6 | 1.233 | 3.459 | 22 | 718.64 |
| 0.482 | 5 | 0.6 | 1.224 | 3.908 | 9 | 291.8 |
| 0.919 | 6 | 0.6 | 1.223 | 4.785 | 10 | 323.21 |
| 1.824 | 7 | 0.59 | 1.224 | 6.024 | 11 | 361.01 |
| 2.098 | 8 | 0.59 | 1.205 | 6.321 | 11 | 356.32] |

Figure 13:
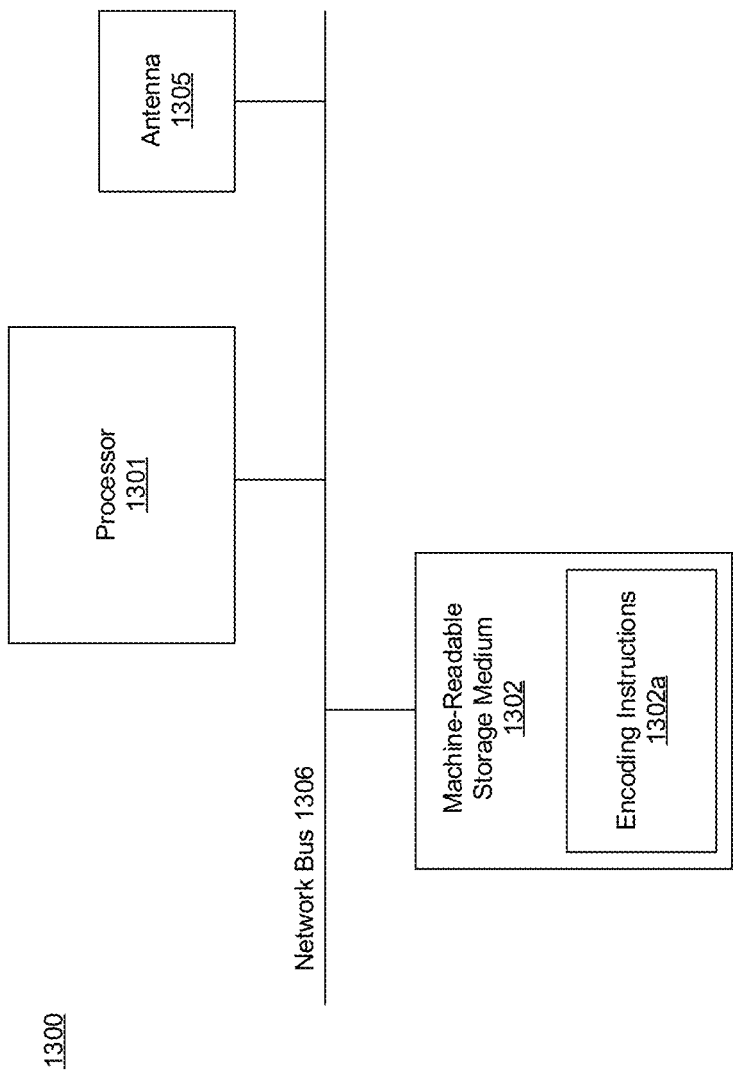
FIG. 13 illustrates a sensor node with machine readable storage medium having instructions to perform continuous CS of signals, according to some embodiments of the disclosure.

FIG. 13 illustrates a sensor node 1300 (e.g., part of 201) with machine readable storage medium 1302 having instructions to perform continuous compressive sensing of signals, according to some embodiments of the disclosure. It is pointed out that those elements of FIG. 13 having the same reference numbers (or names) as the elements of any other figure can operate or function in any manner similar to that described, but are not limited to such.

In some embodiments, sensor node 1300/201 comprises a low power Processor 1301 (e.g., a Digital Signal Processor (DSP), an Application Specific Integrated Circuit (ASCI), a general purpose Central Processing Unit (CPU)), Machine-Readable Storage Medium 1302 (also referred to as tangible machine readable medium), Antenna 1305 (e.g., Antenna 202/208) and Network Bus 1306. In some embodiments, the various logic blocks of sensor node 1300/201 are coupled together via Network Bus 1306. Any suitable protocol may be used to implement Network Bus 1306. In some embodiments, Machine-Readable Storage Medium 1302 includes Encoding Instructions 1302a (also referred to as the program software code/instructions) for encoding a padded digital stream as described with reference to various embodiments and flowcharts.

Program software code/instructions 1302a associated with flowchart 500 and executed to implement embodiments of the disclosed subject matter may be implemented as part of an operating system or a specific application, component, program, object, module, routine, or other sequence of instructions or organization of sequences of instructions referred to as "program software code/instructions," "operating system program software code/instructions," "application program software code/instructions," or simply "software" or firmware embedded in processor. In some embodiments, the program software code/instructions associated with flowchart 500 are executed by sensor node 1300 (such as shown in FIG. 2).

Referring back to FIG. 13, in some embodiments, the program software code/instructions 1302a associated with flowchart 500 are stored in a computer executable storage medium 1302 and executed by Processor 1301. Here, computer executable storage medium 1302 is a tangible machine readable medium that can be used to store program software code/instructions and data that, when executed by a computing device, causes one or more processors (e.g., Processor 1301) to perform a method(s) as may be recited in one or more accompanying claims directed to the disclosed subject matter.

The tangible machine readable medium 1302 may include storage of the executable software program code/instructions 1302a and data in various tangible locations, including for example ROM, volatile RAM, non-volatile memory and/or cache and/or other tangible memory as referenced in the present application. Portions of this program software code/instructions 1302a and/or data may be stored in any one of these storage and memory devices. Further, the program software code/instructions can be obtained from other storage, including, e.g., through centralized servers or peer to peer networks and the like, including the Internet. Different portions of the software program code/instructions and data can be obtained at different times and in different communication sessions or in the same communication session.

The software program code/instructions 1302a (associated with flowchart 500 and other embodiments) and data can be obtained in their entirety prior to the execution of a respective software program or application by the computing device. Alternatively, portions of the software program code/instructions 1302a and data can be obtained dynamically, e.g., just in time, when needed for execution. Alternatively, some combination of these ways of obtaining the software program code/instructions 1302a and data may occur, e.g., for different applications, components, programs, objects, modules, routines or other sequences of instructions or organization of sequences of instructions, by way of example. Thus, it is not required that the data and instructions be on a tangible machine readable medium in entirety at a particular instance of time.

Examples of tangible computer-readable media 1302 include but are not limited to recordable and non-recordable type media such as volatile and non-volatile memory devices, read only memory (ROM), random access memory (RAM), flash memory devices, floppy and other removable disks, magnetic storage media, optical storage media (e.g., Compact Disk Read-Only Memory (CD ROMS), Digital Versatile Disks (DVDs), etc.), among others. The software program code/instructions may be temporarily stored in digital tangible communication links while implementing electrical, optical, acoustical or other forms of propagating signals, such as carrier waves, infrared signals, digital signals, etc. through such tangible communication links.

In general, tangible machine readable medium 1302 includes any tangible mechanism that provides i.e., stores and/or transmits in digital form, e.g., data packets) information in a form accessible by a machine (i.e., a computing device), which may be included, e.g., in a communication device, a computing device, a network device, a personal digital assistant, a manufacturing tool, a mobile communication device, whether or not able to download and run applications and subsidized applications from the communication network, such as the Internet, e.g., an iPhone®, Galaxy®, Blackberry® Droid®, or the like, or any other device including a computing device. In one embodiment, processor-based system is in a form of or included within a PDA, a cellular phone, a notebook computer, a tablet, a game console, a set top box, an embedded system, a TV, a personal desktop computer, etc. Alternatively, the traditional communication applications and subsidized application(s) may be used in some embodiments of the disclosed subject matter.

Figure 14:
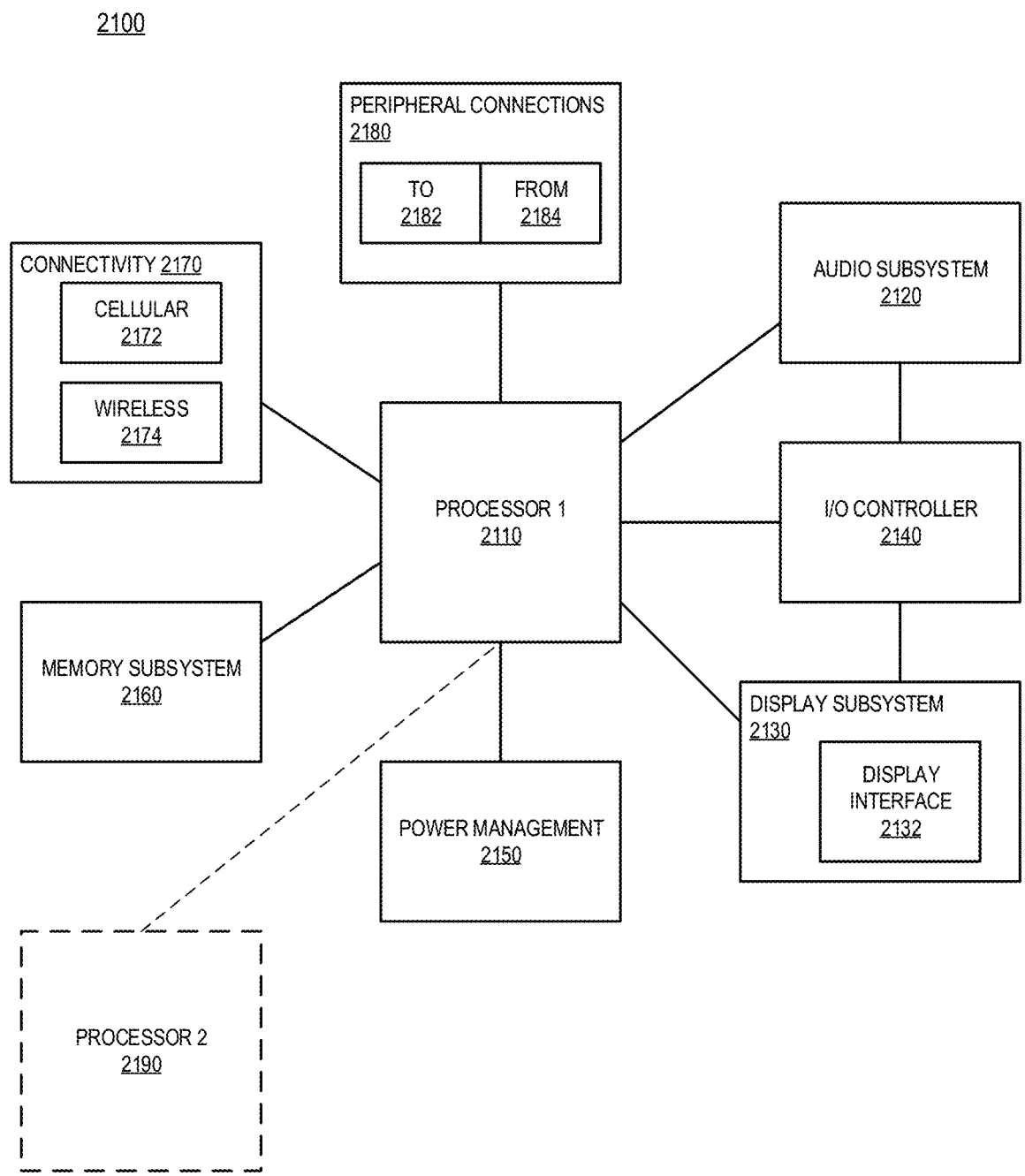
FIG. 14 illustrates a smart device or a computer system or a SoC (System-on-Chip) with apparatus and/or machine executable instructions to reconstruct the continuous CS signals, according to some embodiments.

FIG. 14 illustrates a smart device or a computer system or a SoC (System-on-Chip) 2100 with apparatus and/or machine executable instructions to reconstruct the continuously compressed signals, according to some embodiments. It is pointed out that those elements of FIG. 14 having the same reference numbers (or names) as the elements of any other figure can operate or function in any manner similar to that described, but are not limited to such.

FIG. 14 illustrates a block diagram of an embodiment of a mobile device in which flat surface interface connectors could be used. In some embodiments, computing device 2100 represents a mobile computing device, such as a computing tablet, a mobile phone or smart-phone, a wireless-enabled e-reader, or other wireless mobile device. It will be understood that certain components are shown generally, and not all components of such a device are shown in computing device 2100.

In some embodiments, computing device 2100 includes a first processor 2110 with apparatus and/or machine executable instructions to reconstruct the continuously compressed signals, according to some embodiments discussed. Other blocks of the computing device 2100 may also include apparatus and/or machine executable instructions to reconstruct the continuously compressed signals, according to some embodiments. The various embodiments of the present disclosure may also comprise a network interface within 2170 such as a wireless interface so that a system embodiment may be incorporated into a wireless device, for example, cell phone or personal digital assistant.

In one embodiment, processor 2110 (and/or processor 2190) can include one or more physical devices, such as microprocessors, application processors, microcontrollers, programmable logic devices, or other processing means. The processing operations performed by processor 2110 include the execution of an operating platform or operating system on which applications and/or device functions are executed. The processing operations include operations related to I/O (input/output) with a human user or with other devices, operations related to power management, and/or operations related to connecting the computing device 2100 to another device. The processing operations may also include operations related to audio I/O and/or display I/O.

In one embodiment, computing device 2100 includes audio subsystem 2120, which represents hardware (e.g., audio hardware and audio circuits) and software (e.g., drivers, codecs) components associated with providing audio functions to the computing device. Audio functions can include speaker and/or headphone output, as well as microphone input. Devices for such functions can be integrated into computing device 2100, or connected to the computing device 2100. In one embodiment, a user interacts with the computing device 2100 by providing audio commands that are received and processed by processor 2110.

Display subsystem 2130 represents hardware (e.g., display devices) and software (e.g., drivers) components that provide a visual and/or tactile display for a user to interact with the computing device 2100. Display subsystem 2130 includes display interface 2132, which includes the particular screen or hardware device used to provide a display to a user. In one embodiment, display interface 2132 includes logic separate from processor 2110 to perform at least some processing related to the display. In one embodiment, display subsystem 2130 includes a touch screen (or touch pad) device that provides both output and input to a user.

I/O controller 2140 represents hardware devices and software components related to interaction with a user. I/O controller 2140 is operable to manage hardware that is part of audio subsystem 2120 and/or display subsystem 2130. Additionally, I/O controller 2140 illustrates a connection point for additional devices that connect to computing device 2100 through which a user might interact with the system. For example, devices that can be attached to the computing device 2100 might include microphone devices, speaker or stereo systems, video systems or other display devices, keyboard or keypad devices, or other I/O devices for use with specific applications such as card readers or other devices.

As mentioned above, I/O controller 2140 can interact with audio subsystem 2120 and/or display subsystem 2130. For example, input through a microphone or other audio device can provide input or commands for one or more applications or functions of the computing device 2100. Additionally, audio output can be provided instead of, or in addition to display output. In another example, if display subsystem 2130 includes a touch screen, the display device also acts as an input device, which can be at least partially managed by I/O controller 2140. There can also be additional buttons or switches on the computing device 2100 to provide I/O functions managed by I/O controller 2140.

In one embodiment, I/O controller 2140 manages devices such as accelerometers, cameras, light sensors or other environmental sensors, or other hardware that can be included in the computing device 2100. The input can be part of direct user interaction, as well as providing environmental input to the system to influence its operations (such as filtering for noise, adjusting displays for brightness detection, applying a flash for a camera, or other features).

In one embodiment, computing device 2100 includes power management 2150 that manages battery power usage, charging of the battery, and features related to power saving operation. Memory subsystem 2160 includes memory devices for storing information in computing device 2100. Memory can include nonvolatile (state does not change if power to the memory device is interrupted) and/or volatile (state is indeterminate if power to the memory device is interrupted) memory devices. Memory subsystem 2160 can store application data, user data, music, photos, documents, or other data, as well as system data (whether long-term or temporary) related to the execution of the applications and functions of the computing device 2100.

Elements of embodiments are also provided as a machine-readable medium (e.g., memory 2160) for storing the computer-executable instructions (e.g., instructions to implement any other processes discussed herein). The machine-readable medium (e.g., memory 2160) may include, but is not limited to, flash memory, optical disks. CD-ROMs, DVD ROMs, RAMs, EPROMs, EEPROMs, magnetic or optical cards, phase change memory (PCM), or other types of machine-readable media suitable for storing electronic or computer-executable instructions. For example, embodiments of the disclosure may be downloaded as a computer program (e.g., BIOS) which may be transferred from a remote computer (e.g., a server) to a requesting computer (e.g., a client) by way of data signals via a communication link (e.g., a modem or network connection).

Connectivity 2170 includes hardware devices (e.g., wireless and/or wired connectors and communication hardware) and software components (e.g., drivers, protocol stacks) to enable the computing device 2100 to communicate with external devices. The computing device 2100 could be separate devices, such as other computing devices, wireless access points or base stations, as well as peripherals such as headsets, printers, or other devices.

Connectivity 2170 can include multiple different types of connectivity. To generalize, the computing device 2100 is illustrated with cellular connectivity 2172 and wireless connectivity 2174. Cellular connectivity 2172 refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, or other cellular service standards. Wireless connectivity (or wireless interface) 2174 refers to wireless connectivity that is not cellular, and can include personal area networks (such as Bluetooth, Near Field, etc.), local area networks (such as Wi-Fi), and/or wide area networks (such as WiMax), or other wireless communication.

In some embodiments, Peripheral connections 2180 include hardware interfaces and connectors, as well as software components (e.g., drivers, protocol stacks) to make peripheral connections. It will be understood that the computing device 2100 could be a peripheral device ("to" 2182) to other computing devices, as well as have peripheral devices ("from" 2184) connected to it. The computing device 2100 commonly has a "docking" connector to connect to other computing devices for purposes such as managing (e.g., downloading and/or uploading, changing, synchronizing) content on computing device 2100. Additionally, a docking connector can allow computing device 2100 to connect to certain peripherals that allow the computing device 2100 to control content output, for example, to audiovisual or other systems.

In addition to a proprietary docking connector or other proprietary connection hardware, the computing device 2100 can make peripheral connections 2180 via common or standards-based connectors. Common types can include a Universal Serial Bus (USB) connector (which can include any of a number of different hardware interfaces), DisplayPort including MiniDisplayPort (MDP), High Definition Multimedia Interface (HDMI), Firewire, or other types.

Reference in the specification to "an embodiment," "one embodiment," "some embodiments," or "other embodiments" means that a particular feature, structure, or characteristic described in connection with the embodiments is included in at least some embodiments, but not necessarily all embodiments. The various appearances of "an embodiment," "one embodiment," or "some embodiments" are not necessarily all referring to the same embodiments. If the specification states a component, feature, structure, or characteristic "may," "might," or "could" be included, that particular component, feature, structure, or characteristic is not required to be included. If the specification or claim refers to "a" or "an" element, that does not mean there is only one of the elements. If the specification or claims refer to "an additional" element, that does not preclude there being more than one of the additional element.

Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive.

While the disclosure has been described in conjunction with specific embodiments thereof, many alternatives, modifications and variations of such embodiments will be apparent to those of ordinary skill in the art in light of the foregoing description. The embodiments of the disclosure are intended to embrace all such alternatives, modifications, and variations as to fall within the broad scope of the appended claims.

In addition, well known power/ground connections to integrated circuit (IC) chips and other components may or may not be shown within the presented figures, for simplicity of illustration and discussion, and so as not to obscure the disclosure. Further, arrangements may be shown in block diagram form in order to avoid obscuring the disclosure, and also in view of the fact that specifics with respect to implementation of such block diagram arrangements are highly dependent upon the platform within which the present disclosure is to be implemented (i.e., such specifics should be well within purview of one skilled in the art). Where specific details (e.g., circuits) are set forth in order to describe example embodiments of the disclosure, it should be apparent to one skilled in the art that the disclosure can be practiced without, or with variation of, these specific details. The description is thus to be regarded as illustrative instead of limiting.

The following examples pertain to further embodiments. In one example, a machine-readable storage media is provided having instruction stored thereon, that when executed, cause one or more processors to perform an operation comprising: receive an input signal from a sensor; convert the input signal to a digital stream; and symmetrically pad on either ends of the digital stream with a portion of the digital stream to form a padded digital stream. In some embodiments, the machine-readable storage media has further instruction stored thereon, that when executed, cause the one or more processors to perform a further operation comprising: select a part of the digital stream; transmit the selected part of the digital stream to another device; and receive one or more configuration parameters from the other device in response to the transmitted selected part of the digital stream.

In some embodiments, the machine-readable storage media has further instruction stored thereon, that when executed, cause the one or more processors to perform a further operation comprising: prior to symmetrically padding on either ends of the digital stream, compute a number of elements to be padded using the one or more configuration parameters. In some embodiments, the number of elements determines the portion of the digital stream. In some embodiments, at least one of the one or more configuration parameters is dynamically received from the other device.

In some embodiments, at least one of the one or more configuration parameters is periodically received from the other device. In some embodiments, at least one of the one or more configuration parameters is a compression ratio. In some embodiments, the machine-readable storage media has further instruction stored thereon, that when executed, cause the one or more processors to perform a further operation comprising: construct an encoding matrix using the one or more configuration parameters; and encode the padded digital stream using the encoding matrix to generate compressed padded data. In some embodiments, the encoding matrix is a Binary Permuted Block Diagonal (BPBD) matrix.

In some embodiments, the machine-readable storage media has further instruction stored thereon, that when executed, cause the one or more processors to perform a further operation comprising: transmit the compressed padded data to the other device for processing. In some embodiments, the machine-readable storage media of has further instruction stored thereon, that when executed, cause the one or more processors to perform a further operation comprising: identify types of at least two sensors including the sensor; aggregate information about the types of the at least two sensors; transmit the aggregated information to another device; and receive configuration parameters for each of the at least two sensors from the other device.

In some embodiments, the machine-readable storage media has further instruction stored thereon, that when executed, cause the one or more processors to perform a further operation comprising: transmit a signal, to another device, indicating a type of the sensor or a type of the input signal; and receive one or more configuration parameters from the other device in response to the transmitted signal, wherein the one or more configuration parameters depend on the type of the sensor or the type of the input signal. In some embodiments, at least one of the one or more configuration parameters is a compression ratio for encoding a matrix of the padded digital stream.

In another example, a sensor is provided which comprises: a receiver to process an input signal; an analog-to-digital converter to convert the processed input signal to a digital stream; logic which is operable to symmetrically pad on either ends of the digital stream with a portion of the digital stream to form a padded digital stream; logic which is operable to construct an encoding matrix by applying one or more configuration parameters; and an encoder to encode the padded digital by applying the encoded matrix.

In some embodiments, at least one of the one or more configuration parameters is a compression ratio. In some embodiments, the encoding matrix is a Binary Permuted Block Diagonal (BPBD) matrix. In some embodiments, the sensor comprises: an antenna; and a transmitter to transmit the encoded padded digital stream via the antenna to another device for processing.

In some embodiments, the sensor comprises an antenna to transmit a selected part of the digital stream, to another device. In some embodiments, the antenna is to receive the one or more configuration parameters for the other device in response to transmitting the selected part of the digital stream. In some embodiments, the receiver includes: a photodiode to receive the input signal and to generate a corresponding current; and a circuit to convert the corresponding current to the processed input signal.

In another example, a method is provided which comprises: receiving an input signal from a sensor; converting the input signal to a digital stream; and symmetrically padding on either ends of the digital stream with a portion of the digital stream to form a padded digital stream. In some embodiments, the method further comprises: selecting a part of the digital stream; transmitting the selected part of the digital stream to another device; and receiving one or more configuration parameters from the other device in response to the transmitted selected part of the digital stream.

In some embodiments, the method comprises: prior to symmetrically padding on either ends of the digital stream, computing a number of elements to be padded using the one or more configuration parameters, wherein the number of elements determines the portion of the digital stream. In some embodiments, at least one of the one or more configuration parameters is a compression ratio. In some embodiments, the method comprises: constructing an encoding matrix using the one or more configuration parameters; and encoding the padded digital stream using the encoding matrix to generate compressed padded data. In some embodiments, the matrix is a Binary Permuted Block Diagonal (BPBD) matrix.

In another example, an apparatus is provided which comprises: means for receiving an input signal; means for converting the input signal to a digital stream; and means symmetrically padding on either ends of the digital stream with a portion of the digital stream to form a padded digital stream. In some embodiments, the apparatus further comprises: means for selecting a part of the digital stream; means for transmitting the selected part of the digital stream to another device; and means for receiving one or more configuration parameters from the other device in response to the transmitted selected part of the digital stream.

In some embodiments, the apparatus comprises: means for computing, prior to symmetrically padding on either ends of the digital stream, a number of elements to be padded using the one or more configuration parameters, wherein the number of elements determines the portion of the digital stream. In some embodiments, at least one of the one or more configuration parameters is a compression ratio. In some embodiments, the apparatus comprises: means for constructing an encoding matrix using the one or more configuration parameters; and means for encoding the padded digital stream using the encoding matrix to generate compressed padded data. In some embodiments, the matrix is a Binary Permuted Block Diagonal (BPBD) matrix.

Specifics in the examples may be used anywhere in one or more embodiments. All optional features of the apparatus described herein may also be implemented with respect to a method or process.

An abstract is provided that will allow the reader to ascertain the nature and gist of the technical disclosure. The abstract is submitted with the understanding that it will not be used to limit the scope or meaning of the claims. The following claims are hereby incorporated into the detailed description, with each claim standing on its own as a separate embodiment.

We claim:

1. Non-transitory machine-readable storage media having instruction stored thereon, that when executed, cause one or more processors to perform an operation comprising:

receive an input signal from a sensor;
convert the input signal to a digital stream; and
symmetrically pad on either ends of the digital stream with a portion of the digital stream to form a padded digital stream, wherein the portion of the digital stream is non-zero, and wherein the portion of the digital stream is a sequence of zeros and ones which is identical to a sequence of zeros of ones in the digital stream.

2. The non-transitory machine-readable storage media of claim 1 having further instruction stored thereon, that when executed, cause the one or more processors to perform a further operation comprising:
select a part of the digital stream;
transmit the selected part of the digital stream to another device; and
receive one or more configuration parameters from the other device in response to the transmitted selected part of the digital stream.

3. The non-transitory machine-readable storage media of claim 2 having further instruction stored thereon, that when executed, cause the one or more processors to perform a further operation comprising:
prior to symmetrically padding on either ends of the digital stream, compute a number of elements to be padded using the one or more configuration parameters.

4. The non-transitory machine-readable storage media of claim 3, wherein number of elements determines the portion of the digital stream.

5. The non-transitory machine-readable storage media of claim 2, wherein at least one of the one or more configuration parameters is dynamically received from the other device.

6. The non-transitory machine-readable storage media of claim 2, wherein at least one of the one or more configuration parameters is periodically received from the other device.

7. The non-transitory machine-readable storage media of claim 2, wherein at least one of the one or more configuration parameters is a compression ratio.

8. The non-transitory machine-readable storage media of claim 3 having further instruction stored thereon, that when executed, cause the one or more processors to perform a further operation comprising:
construct an encoding matrix using the one or more configuration parameters; and
encode the padded digital stream using the encoding matrix to generate compressed padded data.

9. The non-transitory machine-readable storage media of claim 8, wherein the encoding matrix is a Binary Permuted Block Diagonal (BPBD) matrix.

10. The non-transitory machine-readable storage media of claim 9 having further instruction stored thereon, that when executed, cause the one or more processors to perform a further operation comprising:
transmit the compressed padded data to the other device for processing.

11. The non-transitory machine-readable storage media of claim 1 having further instruction stored thereon, that when executed, cause the one or more processors to perform a further operation comprising:
identify types of at least two sensors including the sensor;
aggregate information about the types of the at least two sensors;
transmit the aggregated information to another device; and
receive configuration parameters for each of the at least two sensors from the other device.

12. The non-transitory machine-readable storage media of claim 1 having further instruction stored thereon, that when executed, cause the one or more processors to perform a further operation comprising:
transmit a signal, to another device, indicating a type of the sensor or a type of the input signal; and
receive one or more configuration parameters from the other device in response to the transmitted signal, wherein the one or more configuration parameters depend on the type of the sensor or the type of the input signal.

13. The non-transitory machine-readable storage media of claim 12, wherein at least one of the one or more configuration parameters is a compression ratio for encoding a matrix of the padded digital stream.

14. A sensor comprising:
a receiver to process an input signal;
an analog-to-digital converter to convert the processed input signal to a digital stream;
logic which is operable to symmetrically pad on either ends of the digital stream with a portion of the digital stream to form a padded digital stream, wherein the portion of the digital stream is non-zero, and wherein the portion of the digital stream is a sequence of zeros and ones which is identical to a sequence of zeros of ones in the digital stream;
logic which is operable to construct an encoding matrix by application of one or more configuration parameters; and
an encoder to encode the padded digital by application of the encoded matrix.

15. The sensor of claim 14, wherein at least one of the one or more configuration parameters is a compression ratio.

16. The sensor of claim 14, wherein the encoding matrix is a Binary Permuted Block Diagonal (BPBD) matrix.

17. The sensor of claim 14 comprises:
an antenna; and
a transmitter to transmit the encoded padded digital stream via the antenna to another device.

18. The sensor of claim 14 comprises an antenna to transmit a selected part of the digital stream, to another device.

19. The sensor of claim 18, wherein the antenna is to receive the one or more configuration parameters for the other device in response to transmission of the selected part of the digital stream.

20. The sensor of claim 14, wherein the receiver includes:
a photodiode to receive the input signal and to generate a corresponding current; and
a circuit to convert the corresponding current to the processed input signal.

21. A method comprising:
receiving an input signal from a sensor;
converting the input signal to a digital stream; and
symmetrically padding on either ends of the digital stream with a portion of the digital stream to form a padded digital stream, wherein the portion of the digital stream is non-zero, and wherein the portion of the digital stream is a sequence of zeros and ones which is identical to a sequence of zeros of ones in the digital stream.

22. The method of claim 21 further comprises:
selecting a part of the digital stream;
transmitting the selected part of the digital stream to another device; and receiving one or more configuration parameters from the other device in response to the transmitted selected part of the digital stream.

23. The method of claim 22 comprises: prior to symmetrically padding on either ends of the digital stream, computing a number of elements to be padded using the one or more configuration parameters, wherein the number of elements determines the portion of the digital stream.

24. The method of claim 21, wherein at least one of the one or more configuration parameters is a compression ratio.

25. The method of claim 21 comprises:
- constructing an encoding matrix using the one or more configuration parameters; and
- encoding the padded digital stream using the encoding matrix to generate compressed padded data, wherein the matrix is a Binary Permuted Block Diagonal (BPBD) matrix.

\* \* \* \* \*